(12) United States Patent
Hajela et al.

(10) Patent No.: US 12,059,342 B2
(45) Date of Patent: Aug. 13, 2024

(54) INTRAOCULAR LENS MATERIALS AND COMPONENTS

(71) Applicant: Alcon Inc., Fribourg (CH)

(72) Inventors: Sharad Hajela, San Carlos, CA (US); Gomaa Abdelsadek, San Diego, CA (US); Sean Halenbeck, Los Altos, CA (US)

(73) Assignee: Alcon Inc., Fribourg (CH)

( * ) Notice: Subject to any disclaimer, the term of this patent is extended or adjusted under 35 U.S.C. 154(b) by 491 days.

(21) Appl. No.: 16/834,787

(22) Filed: Mar. 30, 2020

(65) Prior Publication Data

US 2020/0246134 A1  Aug. 6, 2020

Related U.S. Application Data

(63) Continuation of application No. 15/575,405, filed as application No. PCT/US2016/037055 on Jun. 10, 2016, now abandoned.

(60) Provisional application No. 62/173,877, filed on Jun. 10, 2015, provisional application No. 62/321,704, filed on Apr. 12, 2016.

(51) Int. Cl.
| | |
|---|---|
| *A61F 2/16* | (2006.01) |
| *A61L 27/18* | (2006.01) |
| *C08G 77/34* | (2006.01) |
| *C09J 4/00* | (2006.01) |
| *C09J 4/06* | (2006.01) |
| *G02C 7/08* | (2006.01) |

(52) U.S. Cl.
CPC ............. *A61F 2/1613* (2013.01); *A61F 2/16* (2013.01); *A61F 2/1635* (2013.01); *A61L 27/18* (2013.01); *C08G 77/34* (2013.01); *C09J 4/00* (2013.01); *C09J 4/06* (2013.01); *G02C 7/085* (2013.01); *A61F 2240/00* (2013.01); *A61F 2240/001* (2013.01)

(58) Field of Classification Search
None
See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |

(Continued)

FOREIGN PATENT DOCUMENTS

| | | |
|---|---|---|
| CN | 1283974 | 2/2001 |
| CN | 1367667 | 9/2002 |

(Continued)

OTHER PUBLICATIONS

EGM-002 Product Description (Year: 2023).*

(Continued)

*Primary Examiner* — Peter A Salamon
(74) *Attorney, Agent, or Firm* — Levine Bagade Han LLP

(57) ABSTRACT

Materials and methods of manufacturing intraocular lenses, including polymeric materials for the intraocular lenses, fluids for intraocular lenses, and adhesives for intraocular lenses. The intraocular lenses can include an optic portion and a peripheral region in fluid communication.

9 Claims, 7 Drawing Sheets

(56) References Cited

U.S. PATENT DOCUMENTS

| | | |
|---|---|---|
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turley |
| 4,902,293 A | 2/1990 | Feaster |
| 4,913,536 A | 4/1990 | Barnea |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,169,920 A | 12/1992 | Okawa |
| 5,426,166 A | 6/1995 | Usifer et al. |
| 5,767,669 A | 6/1998 | Hansen et al. |
| 6,140,438 A | 10/2000 | Ojio et al. |
| 7,378,382 B2 | 5/2008 | Serobian et al. |
| 7,416,300 B2 | 8/2008 | Wei et al. |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,637,947 B2 | 12/2009 | Smith et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,776,088 B2 | 8/2010 | Shadduck |
| 7,878,655 B2 | 2/2011 | Salvati et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 7,988,293 B2 | 8/2011 | Raymond et al. |
| 8,048,155 B2 | 11/2011 | Shadduck |
| 8,158,712 B2 * | 4/2012 | Your ............... A61L 27/16 623/6.37 |
| 8,162,927 B2 | 4/2012 | Peyman |
| 8,241,355 B2 | 8/2012 | Brady et al. |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,377,125 B2 | 2/2013 | Kellan |
| 8,425,599 B2 | 4/2013 | Shadduck |
| 8,447,086 B2 | 5/2013 | Hildebrand et al. |
| 8,454,688 B2 | 6/2013 | Esch et al. |
| 8,480,734 B2 | 7/2013 | Kellan et al. |
| 8,523,941 B2 | 9/2013 | Ichinohe et al. |
| 8,574,239 B2 | 11/2013 | Ichinohe et al. |
| 8,613,766 B2 | 12/2013 | Richardson et al. |
| 8,632,589 B2 | 1/2014 | Helmy |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,005,282 B2 | 4/2015 | Chang et al. |
| 9,034,035 B2 | 5/2015 | Betser et al. |
| 9,044,317 B2 | 6/2015 | Hildebrand et al. |
| 9,277,987 B2 | 3/2016 | Smiley et al. |
| 9,326,846 B2 | 5/2016 | Devita Gerardi et al. |
| 9,329,306 B2 | 5/2016 | Huang et al. |
| 9,456,895 B2 | 10/2016 | Shadduck |
| 9,610,155 B2 | 4/2017 | Matthews |
| 9,622,855 B2 | 4/2017 | Portney et al. |
| 9,693,858 B2 | 7/2017 | Hildebrand et al. |
| 9,795,473 B2 | 10/2017 | Smiley et al. |
| 9,855,137 B2 | 1/2018 | Smiley et al. |
| 9,855,139 B2 | 1/2018 | Matthews et al. |
| 9,872,762 B2 | 1/2018 | Scholl et al. |
| 9,872,763 B2 | 1/2018 | Smiley et al. |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236375 A1 | 12/2003 | Salamone et al. |
| 2003/0236376 A1 | 12/2003 | Kindt-larsen et al. |
| 2004/0001180 A1 | 1/2004 | Epstein |

(56) References Cited

U.S. PATENT DOCUMENTS

| | | |
|---|---|---|
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | Mcnicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0230203 A1 | 11/2004 | Yaguchi |
| 2005/0021139 A1 | 1/2005 | Shadduck |
| 2005/0090612 A1* | 4/2005 | Soane .............. C08F 8/00 524/800 |
| 2005/0113911 A1 | 5/2005 | Peyman |
| 2005/0125000 A1 | 6/2005 | Tourrette et al. |
| 2005/0131535 A1 | 6/2005 | Woods |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0241752 A1 | 10/2006 | Israel |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0027538 A1 | 2/2007 | Aharoni et al. |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0118216 A1 | 5/2007 | Pynson |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0213817 A1 | 9/2007 | Esch et al. |
| 2007/0244561 A1 | 10/2007 | Ben nun |
| 2007/0254005 A1* | 11/2007 | Pathak .............. A61L 27/24 424/423 |
| 2007/0260157 A1 | 11/2007 | Norrby |
| 2008/0004699 A1 | 1/2008 | Ben nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200982 A1* | 8/2008 | Your .............. A61L 27/16 623/6.37 |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2009/0005865 A1 | 1/2009 | Smiley et al. |
| 2009/0076602 A1 | 3/2009 | Ho et al. |
| 2009/0124773 A1 | 5/2009 | Zhou et al. |
| 2009/0149952 A1 | 6/2009 | Shadduck |
| 2009/0228101 A1 | 9/2009 | Zadno-Azizi |
| 2009/0234449 A1 | 9/2009 | Juan et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0319040 A1 | 12/2009 | Khoury |
| 2010/0016963 A1 | 1/2010 | Park |
| 2010/0039709 A1 | 2/2010 | Lo |
| 2010/0063588 A1 | 3/2010 | Park |
| 2010/0069522 A1 | 3/2010 | Linhardt et al. |
| 2010/0094412 A1 | 4/2010 | Wensrich |
| 2010/0131058 A1 | 5/2010 | Shadduck |
| 2010/0131061 A1 | 5/2010 | Callahan et al. |
| 2010/0161049 A1 | 6/2010 | Inoue |
| 2010/0179653 A1 | 7/2010 | Argento et al. |
| 2010/0228344 A1 | 9/2010 | Shadduck |
| 2010/0228346 A1 | 9/2010 | Esch |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2011/0313522 A1 | 12/2011 | Hayes |
| 2011/0313523 A1 | 12/2011 | Hayes |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0202916 A1 | 8/2012 | Laredo et al. |
| 2012/0221102 A1 | 8/2012 | Tanaka et al. |
| 2012/0226351 A1 | 9/2012 | Peyman |
| 2012/0253458 A1 | 10/2012 | Geraghty et al. |
| 2012/0253459 A1 | 10/2012 | Reich et al. |
| 2012/0303119 A1 | 11/2012 | Callahan et al. |
| 2012/0330415 A1 | 12/2012 | Callahan et al. |
| 2013/0053954 A1 | 2/2013 | Rao et al. |
| 2013/0060331 A1 | 3/2013 | Shadduck |
| 2013/0128368 A1 | 5/2013 | Costache et al. |
| 2013/0131794 A1 | 5/2013 | Smiley et al. |
| 2013/0184816 A1 | 7/2013 | Hayes |
| 2013/0250239 A1 | 9/2013 | Hildebrand et al. |
| 2013/0268070 A1 | 10/2013 | Esch et al. |
| 2013/0317607 A1 | 11/2013 | Deboer et al. |
| 2014/0121768 A1 | 5/2014 | Simpson |
| 2014/0142587 A1 | 5/2014 | Walter et al. |
| 2014/0227437 A1 | 8/2014 | Deboer et al. |
| 2014/0228949 A1 | 8/2014 | Argento et al. |
| 2014/0257478 A1 | 9/2014 | Mccafferty |
| 2014/0275362 A1* | 9/2014 | Fenn .............. C09D 133/08 524/88 |
| 2014/0330375 A1 | 11/2014 | Mccafferty |
| 2014/0336757 A1 | 11/2014 | Simonov et al. |
| 2015/0087743 A1 | 3/2015 | Anvar et al. |
| 2015/0151021 A1* | 6/2015 | Jiang .............. G02B 1/043 526/245 |
| 2015/0202041 A1 | 7/2015 | Shadduck |
| 2015/0238310 A1 | 8/2015 | Matthews et al. |
| 2016/0008126 A1 | 1/2016 | Salahieh et al. |
| 2016/0038278 A1 | 2/2016 | Matthews |
| 2016/0058553 A1 | 3/2016 | Salahieh et al. |
| 2016/0106534 A1 | 4/2016 | Deboer et al. |
| 2016/0113761 A1 | 4/2016 | Nishi et al. |
| 2016/0128826 A1 | 5/2016 | Silvestrini et al. |
| 2016/0128827 A1 | 5/2016 | Zhao |
| 2016/0157996 A1 | 6/2016 | Dolla et al. |
| 2016/0184089 A1 | 6/2016 | Dudee et al. |
| 2016/0184092 A1 | 6/2016 | Smiley et al. |
| 2016/0262875 A1 | 9/2016 | Smith et al. |
| 2017/0020662 A1 | 1/2017 | Shadduck |
| 2017/0049561 A1 | 2/2017 | Smiley et al. |
| 2017/0258581 A1 | 9/2017 | Borja et al. |
| 2017/0290658 A1 | 10/2017 | Hildebrand et al. |
| 2018/0028308 A1 | 2/2018 | Smiley et al. |
| 2018/0125640 A1 | 5/2018 | Smiley et al. |
| 2018/0132997 A1 | 5/2018 | Smiley et al. |

(56) References Cited

U.S. PATENT DOCUMENTS

| | | |
|---|---|---|
| 2018/0147051 A1 | 5/2018 | Scholl et al. |
| 2018/0153682 A1 | 6/2018 | Hajela et al. |
| 2022/0267571 A1* | 8/2022 | Fihri .................. C08J 5/18 |

FOREIGN PATENT DOCUMENTS

| | | |
|---|---|---|
| CN | 1378440 | 11/2002 |
| CN | 1384727 | 12/2002 |
| CN | 101039635 | 9/2007 |
| CN | 101277659 | 10/2008 |
| CN | 101678149 | 3/2010 |
| CN | 102271622 | 12/2011 |
| CN | 202288610 | 7/2012 |
| DE | 102010010430 | 9/2011 |
| EP | 0898972 | 3/1999 |
| EP | 2060243 | 5/2009 |
| EP | 2192934 | 6/2010 |
| FR | 2655841 | 6/1991 |
| FR | 2784575 | 12/2000 |
| JP | 07-044938 | 5/1995 |
| JP | 07-196946 | 8/1995 |
| JP | 08-034855 | 2/1996 |
| JP | 08-501715 | 2/1996 |
| JP | 08-224295 | 9/1996 |
| JP | 08-239479 | 9/1996 |
| JP | 09-165449 | 6/1997 |
| JP | 09-294754 | 11/1997 |
| JP | 10-206609 | 8/1998 |
| JP | 11-047168 | 2/1999 |
| JP | 11-056998 | 3/1999 |
| JP | 1999-056998 | 3/1999 |
| JP | 11-169391 | 6/1999 |
| JP | 11-276509 | 10/1999 |
| JP | 11-332903 | 12/1999 |
| JP | 2001-502592 | 2/2001 |
| JP | 2003-144387 | 5/2003 |
| JP | 2003-144538 | 5/2003 |
| JP | 2003-524503 | 8/2003 |
| JP | 2003-530978 | 10/2003 |
| JP | 2005-517802 | 6/2005 |
| JP | 2006-341094 | 12/2006 |
| JP | 2007-513715 | 5/2007 |
| JP | 2007-518447 | 7/2007 |
| JP | 2008-531069 | 8/2008 |
| JP | 2008-307394 | 12/2008 |
| JP | 2009-034451 | 2/2009 |
| JP | 2008-307394 | 6/2010 |
| JP | 2013-520291 | 6/2013 |
| RU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2005/018504 | 3/2005 |
| WO | WO 2005/084588 | 9/2005 |
| WO | WO 2006/004707 | 1/2006 |
| WO | WO 2006/047383 | 5/2006 |
| WO | WO 2007/005529 | 1/2007 |
| WO | WO 2007/005692 | 1/2007 |
| WO | WO 2007/030095 | 3/2007 |
| WO | WO 2007/061688 | 5/2007 |
| WO | WO 2007/128423 | 11/2007 |
| WO | WO 2007/138564 | 12/2007 |
| WO | WO 2008/103798 | 8/2008 |
| WO | WO 2009/154455 | 12/2009 |
| WO | WO 2011/106435 | 9/2011 |
| WO | WO 2011/119334 | 9/2011 |
| WO | WO 2013/142323 | 9/2013 |
| WO | WO 2014/095611 | 6/2014 |
| WO | WO 2014/152017 | 9/2014 |

OTHER PUBLICATIONS

Baughman et al. "Negative poisson's ratios for extreme states fo matter," *Science*, vol. 288, pp. 2018-2022, Jun. 16, 2000.

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Hildebrand et al.; U.S. Appl. No. 15/760,640 entitled "Intraocular lenses and methods of manufacturing," filed Mar. 16, 2018.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No contractile obligations," *Nature*, vol. 358, pp. 713-714, Dec. 31, 1992.

Langenbucher et al., "Computerized calculation scheme for toric intraocular lenses," *Acta Ophthalmologica Scandinavica*, vol. 82, No. 3, pp. 270-276, Jun. 2004.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

(56) References Cited

OTHER PUBLICATIONS

Qiao et al.; Bio-inspired accommodating fluidic intraocular lens; *Optics Letters*; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wang et al., "Stable extremely-high-damping discrete viscoelastic systems due to native stiffness elements," *Applied Physics Letters*, vol. 84, No. 22, pp. 4451-4453, May 31, 2004.

Wyant et al.; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

\* cited by examiner

INTRAOCULAR LENS MATERIALS AND COMPONENTS

CROSS-REFERENCE TO RELATED APPLICATIONS

This application is a continuation of U.S. patent application Ser. No. 15/575,405, filed Nov. 20, 2017, which is a U.S. national phase application filed under 35 U.S.C. 371 to PCT International Application No. PCT/US2016/037055, filed Jun. 10, 2016, which claims the benefit of priority to U.S. Provisional Application No. 62/173,877, filed Jun. 10, 2015 and also claims the benefit of priority to U.S. Provisional Application No. 62/321,704, filed Apr. 12, 2016, which are incorporated by reference herein.

This application is related to the following applications and patents, and incorporates each of them by reference herein: U.S. Pat. No. 8,900,298, issued Dec. 2, 2004; U.S. Pub. No. 2013/0131794, published May 23, 2013; U.S. Pat. No. 8,158,712, issued Apr. 17, 2012.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Presbyopia is a condition where the eye loses its ability to focus on nearby objects. It is a natural part of aging and often become noticeable for those in their mid-40's and the condition may continue to worsen until about the age of 65. In order for the eye to see nearby objects clearly, the refractive index of the eye lens needs to be increased, or the shape needs to become more convex, to allow bettering focusing on close objects.

In the case of cataracts, which is a major cause of blindness in the world and the most prevalent ocular disease, this visual disability accounts for more than 8 million physician office visits per year. When the disability from cataracts affects or alters an individual's activities of daily living, surgical lens removal with intraocular lens (IOL) implantation is the preferred method of treating the related visual limitations. In the United States, about 2.5 million cataract surgical procedures are performed annually, making it the most common surgery for Americans over the age of 65. With about 97 percent of cataract surgery patients receiving intraocular lens implants each year, the annual costs for cataract surgery and associated care in the United States is larger than $4 billion.

A cataract is defined as an opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. After cataract surgery, however, the patient typically needs glasses for reading. This is explained by the imaging properties of the human eye, which are facilitated by several optical interfaces.

Apart from the age-related loss of accommodation ability, such loss also has affected IOLs for the treatment of cataracts. Although the research directed at accommodating IOLs has met with some success, the relative complexity and limited efficacy of the methods and apparatus developed to date have prevented widespread commercialization of such devices.

Some intraocular lenses include optics, one or more components of which are polymers. In may be desirable that the polymer have properties that allow the intraocular lens to be deformed to a delivery configuration to enable its implantation in the eye, yet return to a pre-implantation configuration after being implanted in the eye. In addition, it may also be desirable that the polymeric composition have a sufficiently high refractive index.

Some intraocular lenses herein include a fluid therein, such as a silicone fluid. For example, some accommodating IOLs use fluid movement within the IOL, or a change in fluid pressure within the IOL, to effect optical power change in the IOL during accommodation. When fluids such as silicone oil are used in an intraocular lens, the fluid, over time, may tend to swell into the bulk polymeric material of the intraocular lens. This can reduce the amount of silicone oil available to drive the optical power change in the IOL. It is therefore desirable to minimize the amount of swelling into the bulk material. It may also be important to provide silicone oil that does not reduce the response time of the accommodating IOL. It would be desirable for the polymer and/or fluid to be adapted such that swelling of the fluid into the polymeric material is minimized, or even prevented.

For IOLs that include different types of material therein (e.g., cured polymers and silicone oils), there may be a desire to substantially index-match the different types of material (i.e. have the same or substantially the same index of refraction). It may therefore also be beneficial to provide a fluid that has a refractive index that is as close to the refractive index of the bulk polymeric material as possible.

SUMMARY

One aspect of the disclosure is an intraocular lens comprising a polymeric material, the polymeric material comprising: butyl acrylate present in the amount from 2% to 20%, trifluoroethyl methacrylate present in the amount from 10% to 35%, and phenylethyl acrylate present in the amount from 50% to 80%.

In some embodiments the refractive index of the polymeric material is between 1.48 and 1.53. In some embodiments the refractive index of the polymeric material is between 1.50 and 1.53.

In some embodiments the polymeric material defines a fluid channel, the intraocular lens further comprising a silicone oil in the fluid channel. In some embodiments the silicone oil is index matched with the polymeric material. In some embodiments the silicone oil has a polydispersity less than 1.2.

One aspect of the disclosure is a polymeric material for an ophthalmic device, the polymeric material comprising: an alkyl acrylate present in the amount from 3% to 20%; a fluoroacrylate present in the amount from 10% to 35%; and a phenyl acrylate present in the amount from 50% to 80%.

One aspect of the disclosure is an accommodating intraocular lens, comprising: an optic portion adapted to refract light onto a retina, the optic portion comprising a polymeric material; and a silicone oil disposed within the optic portion, wherein the silicone oil has a polydispersity index less than about 1.2.

In some embodiments the mean average molecular weight of the silicone oil is between 4500 and 6500.

In some embodiment the viscosity is no more than 2400 cP.

In some embodiments the silicone oil comprises diphenyl siloxane units.

In some embodiments the silicone oil is made from a cyclotrisiloxane comprising a ratio of two dimethyl siloxane units to one diphenyl siloxane unit.

In some embodiments the refractive index of the silicone oil is between 1.47 and 1.53, optionally between 1.50 and 1.53.

One aspect of the disclosure is an adhesive for an accommodating intraocular lens, wherein the adhesive comprises a first component that is the same or has substantially similar properties as the polymeric material of a first body of the accommodating intraocular lens.

In some embodiments the adhesive comprises a first component that is the same as the polymeric material of the first body of the intraocular lens. In some embodiments the adhesive comprises a first component that comprises monomers that are present in the polymeric material.

In some embodiments the adhesive comprises a second primary component that is a reactive acrylic diluent.

In some embodiments the adhesive comprises a first component that is not the same but is substantially similar to the polymeric material of the first body of the accommodating intraocular lens.

One aspect of the disclosure is a method of manufacturing an accommodating intraocular lens, comprising: curing first and second components of the accommodating intraocular lens; applying an adhesive between the first and second components, wherein the adhesive comprises a first component that is the same, substantially the same, or has substantially similar properties as at least one of the first and second components, the adhesive further comprising a second primary component that is a reactive acrylic diluent.

One aspect of the disclosure is a method of manufacturing a polymeric component of an intraocular lens that includes a plurality of monomers, comprising: forming pre-polymer of the polymer, the pre-polymer comprising the plurality of monomers; and curing the pre-polymer to form the polymeric component.

In some embodiments forming the pre-polymer comprises combining a plurality of monomers with a monomer comprising a hydroxy moiety. The method can further comprise creating a crosslinkable polymer from the pre-polymer, wherein creating the crosslinkable polymer comprises changing the hydroxyl moiety to a methacrylate moiety.

DETAILED DESCRIPTION

The disclosure relates generally to intraocular lenses, optionally accommodating intraocular lenses, and exemplary materials and their properties to impart desired characteristics of the intraocular lens. The intraocular lenses herein are merely examples of intraocular lenses that can include any of the materials herein, and the disclosure is not in any way limited to the exemplary intraocular lenses herein.

In some embodiments the intraocular lens is an accommodating intraocular lens that is adapted to be positioned within a native capsular bag in which a native lens has been removed. In some embodiments a peripheral non-optic portion (i.e., a portion not specifically adapted to focus light on the retina) can be adapted to respond to capsular bag reshaping due to ciliary muscle relaxation and contraction. The response is a deformation of the peripheral portion that causes a fluid disposed within the non-optic portion and the optic portion to be moved between the peripheral portion and an optic portion to change an optical parameter (e.g., power) of the intraocular lens. These embodiments are mere examples of intraocular lenses, optionally accommodating, that include any of the materials or are manufactured using any methods herein.

Figure 1A:
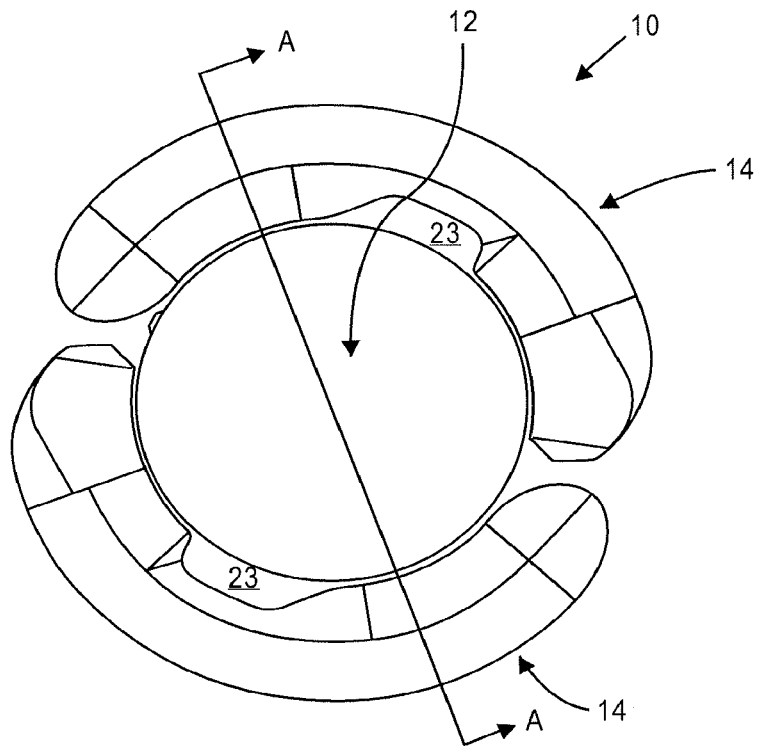
FIGS. 1A and 1B illustrate an exemplary accommodating intraocular lens.
Figure 1B:
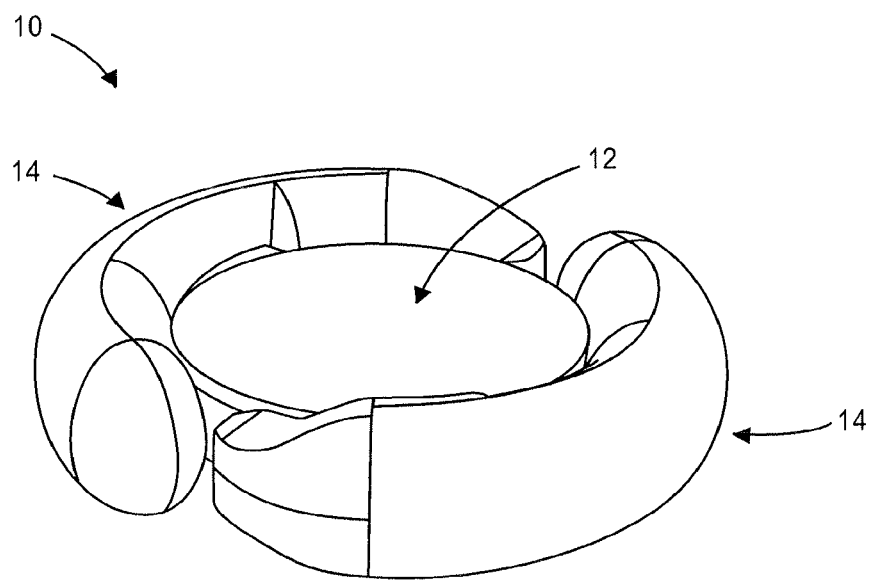

FIG. 1A is a top view illustrating a merely exemplary accommodating intraocular lens 10 that includes optic portion 12 and a peripheral portion that in this embodiment includes first and second haptics 14 coupled to and extending peripherally from optic portion 12. Optic portion 12 is adapted to refract light that enters the eye onto the retina. Haptics 14 are configured to engage a capsular bag and are adapted to deform in response to ciliary muscle related capsular bag reshaping. FIG. 1B is a perspective view of intraocular lens 10 showing optic portion 12 and haptics 14 coupled to optic portion 12.

The haptics are in fluid communication with the optic portion. Each haptic has a fluid chamber that is in fluid communication with an optic chamber in the optic portion. The haptics are formed of a deformable material and are adapted to engage the capsular bag and deform in response to ciliary muscle related capsular bag reshaping. When the haptics deform the volume of the haptic fluid chamber changes, causing a fluid disposed in the haptic fluid chambers and the optic fluid chamber to either move into the optic fluid chamber from the haptic fluid chambers, or into the haptic fluid chambers from the optic fluid chamber. When the volume of the haptic fluid chambers decreases, the fluid is moved into the optic fluid chamber. When the volume of the haptic fluid chamber increases, fluid is moved into the haptic fluid chambers from the optic fluid chamber. The fluid flow into and out of the optic fluid chamber changes the configuration of the optic portion and the power of the intraocular lens.

Figure 1C:
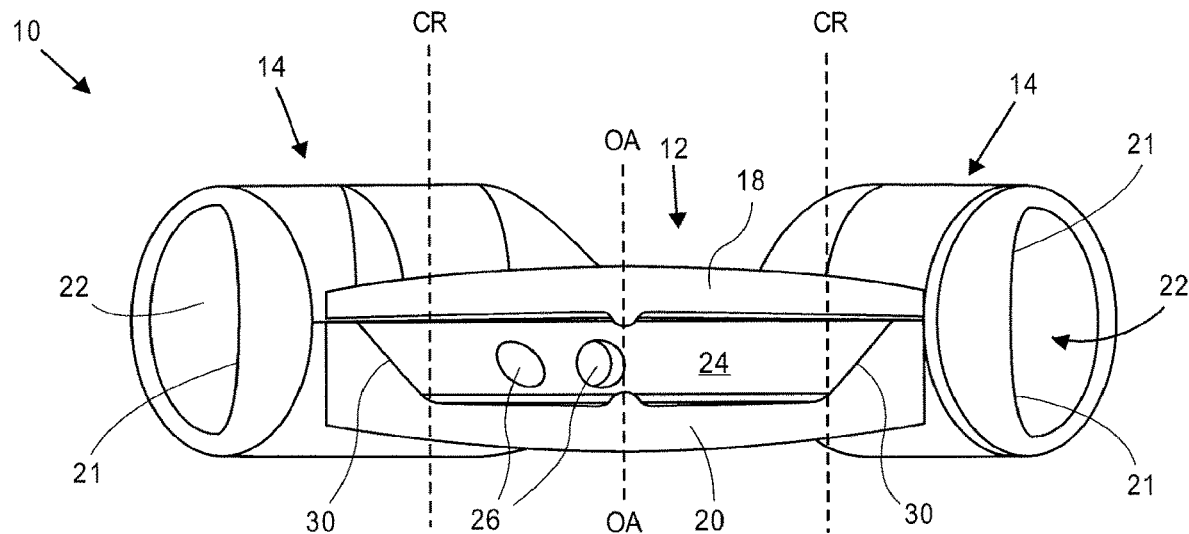
FIG. 1C illustrates a sectional view of the accommodating intraocular lens from FIGS. 1A and 1B.

FIG. 1C is a side sectional view through Section A-A indicated in FIG. 1A. Optic portion 12 includes deformable anterior element 18 secured to deformable posterior element 20. Each haptic 14 includes a fluid chamber 22 that is in fluid communication with optic fluid chamber 24 in optic portion 12. Only the coupling between the haptic 14 to the left in the figure and option portion 12 is shown (although obscured) in the sectional view of FIG. 1C. The haptic fluid chamber 22 to the left in the figure is shown in fluid communication with optic fluid chamber 24 via two apertures 26, which are formed in posterior element 20. The haptic 14 to the right in FIG. 1C is in fluid communication with optic chamber 24 via two additional apertures also formed in posterior element (not shown) substantially 180 degrees from the apertures shown.

Figure 1D:
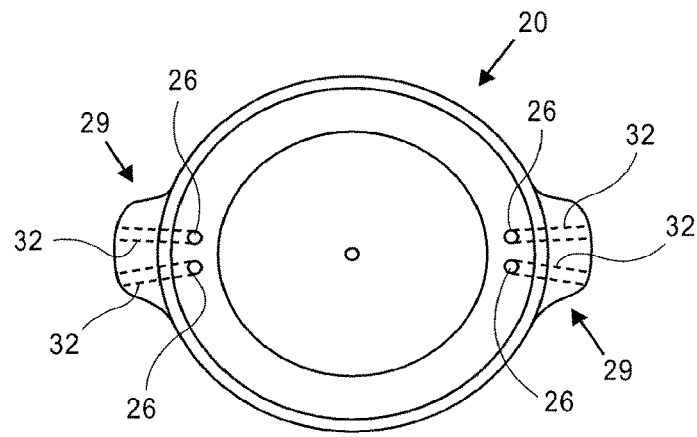
FIG. 1D is a top view of an exemplary posterior element of an accommodating intraocular lens.

FIG. 1D is a top view of posterior element 20 (anterior element 18 and haptics 14 not shown). Posterior element 20 includes buttress portions 29 in which channels 32 are formed. Channels 32 provide fluid communication between optic portion 12 and haptics 14. Apertures 26 are disposed at one end of channels 32. The optic fluid chamber 24 is therefore in fluid communication with a single haptic via two fluid channels. Buttress portions 29 are configured and sized to be disposed within an opening formed in haptics 14 that defines one end of the haptic fluid chamber, as described below. Each of buttress portions 29 includes two channels formed therein. A first channel in a first buttress is in alignment with a first channel in the second buttress. The second channel in the first buttress is in alignment with the second channel in the second buttress.

Figure 1E:
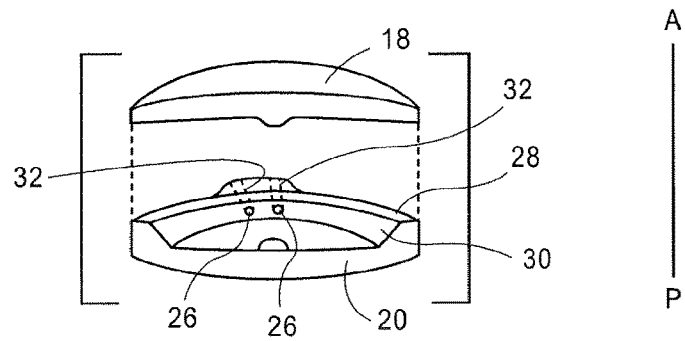
FIG. 1E is a sectional assembly view of an exemplary optic portion of an accommodating intraocular lens.

FIG. 1E is a side assembly view through section A-A of optic portion 12, which includes anterior element 18 and posterior element 20 (haptics not shown for clarity). By including fluid channels 32 in posterior element 20, posterior element 20 needs to have enough structure through which the channels 32 can be formed. Buttress portions 29 provide that structures in which channels 32 can be formed. At its peripheral-most portion posterior element 20 is taller than anterior element 18 in the anterior-to-posterior direction. In alternative embodiments, the channels can be formed in anterior element 18 rather than posterior element 20. The anterior element would include buttress portions 29 or other similar structure to provide structure in which the channels can be formed. In these alternative embodiments the posterior element could be formed similarly to anterior element 18.

As shown in FIG. 1E, posterior element 20 is secured to anterior element 18 at peripheral surface 28, which extends around the periphery of posterior element 20 and is a flat surface. Elements 18 and 20 can be secured together using known biocompatible adhesives, or adhesives as described elsewhere herein, and using known methods or any of the methods of adhering first and second components herein. Anterior element 18 and posterior element 20 can also be formed from one material to eliminate the need to secure two elements together. In some embodiments the diameter of the region at which anterior element 18 and posterior element 20 are secured to one another is about 5.4 mm to about 6 mm in diameter.

The haptics (or other type of peripheral portion, if a separate component) can be adhered to the optic using any of the adhesives herein or any methods of adhering first and second components together described herein.

Figure 2A:
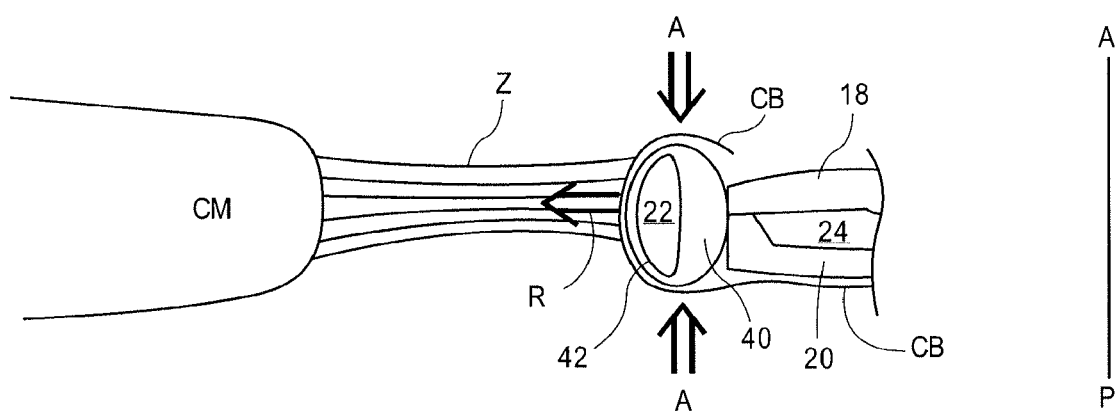
FIGS. 2A and 2B illustrate the deformation of an exemplary haptic in response to exemplary forces.
Figure 2B:
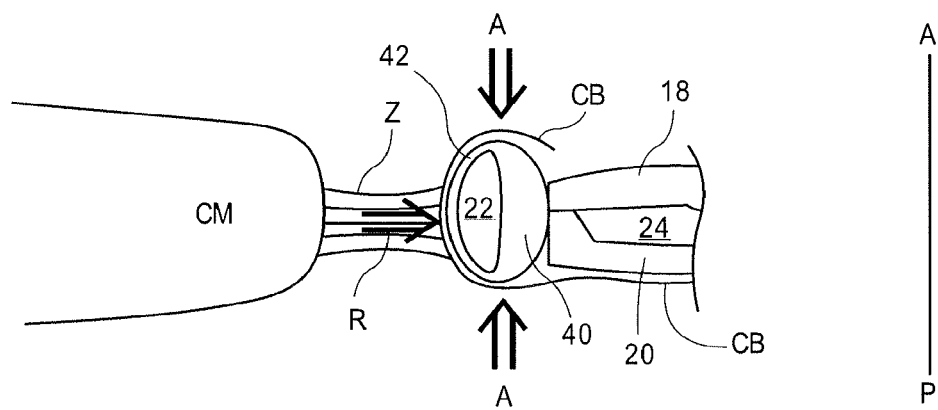

FIGS. 2A and 2B illustrate a merely positioning of an accommodating intraocular lens (which is shown in FIGS. 1A-1E) into an eye, and how it may response to ciliary muscle movement. The deformation of at least a portion of the intraocular lens, and responsiveness of a fluid therein, which are influenced by the materials selected for the AIOL, are illustrated in FIGS. 2A and 2B. The elastic capsular bag "CB" is connected to zonules "Z," which are connected to ciliary muscles "CM." When the ciliary muscles relax, as shown in FIG. 2A, the zonules are stretched. This stretching pulls the capsular bag in the generally radially outward direction due to radially outward forces "R" due to the general equatorial connection location between the capsular bag and the zonules. The zonular stretching causes a general elongation and thinning of the capsular bag. When the native lens is still present in the capsular bag, the native lens becomes flatter (in the anterior-to-posterior direction) and taller in the radial direction, which gives the lens less power. Relaxation of the ciliary muscle, as shown in FIG. 2A, provides for distance vision. When the ciliary muscles contract, however, as occurs when the eye is attempting to focus on near objects, the radially inner portion of the muscles move radially inward, causing the zonules to slacken. This is illustrated in FIG. 2B. The slack in the zonules allows the capsular bag to move towards a generally more curved configuration in which the anterior surface has greater curvature than in the disaccommodated configuration, providing higher power and allowing the eye to focus on near objects. This is generally referred to as "accommodation," and the lens is said to be in an "accommodated" configuration.

The radially outer portion 42 is the portion of the merely exemplary haptic that directly engages the portion of the capsular bag that is connected to the zonules. Outer portion 42 of the haptics is adapted to respond to capsular reshaping forces "R" that are applied generally radially when the zonules relax and stretch. This allows the haptic to deform in response to ciliary muscle related forces (i.e., capsular contraction and relaxation) so that fluid will flow between the haptic and the optic in response to ciliary muscle relaxation and contraction. This is illustrated in FIG. 2B. When the ciliary muscles contract (FIG. 2B), the peripheral region of the elastic capsular bag reshapes and applies radially inward forces "R" on radially outer portion 42 of haptic 14. The radially outer portion 42 is adapted to deform in response to this capsular reshaping. The deformation decreases the volume of fluid channel 22, which forces fluid from haptic chamber 22 into optic chamber 24. This increases the fluid pressure in optic chamber 42. The increase in fluid pressure causes flexible anterior element 18 and flexible posterior element 20 to deform, increasing in curvature, and thus increasing the power of the intraocular lens.

The accommodating intraocular lenses herein can also be adapted to be positioned outside of a native capsular bag. For example, the accommodating intraocular lenses can be adapted to be positioned in front of, or anterior to, the capsular bag after the native lens has been removed or while the native lens is still in the capsular bag, wherein the peripheral portion of the lens is adapted to respond directly with ciliary muscle rather than rely on capsular bag reshaping.

The intraocular lenses described herein, such as the accommodating intraocular lens described in FIGS. 1A-1E, can have one or more components that are polymers. For example, in the example in FIGS. 1A-1E, the anterior and posterior components can be polymeric materials. The peripheral portion (e.g., the haptics) can also be polymers.

The polymeric materials have improved resistance to the diffusion of fluid, relatively high refractive indexes, and are adapted to assume an initial configuration after being deformed during implantation in the human body. While the polymeric materials can be used in a wide variety of applications, the polymers are described herein in their use in an ophthalmic device such as an intraocular lens ("IOL"). While one use of the polymers is for a fluid-driven, accommodating IOL, the polymers can be used in a non-accommodating or non-fluid driven IOL. In addition to an IOL, the polymeric compositions of the present disclosure can also be used in other ophthalmic devices such as, but not limited to, contact lenses, keratoprostheses, capsular bag extension rings, corneal inlays, corneal rings, or other ophthalmic devices. An exemplary alternative use would be in the field of breast implants, such that the polymers can be used as an exterior shell-like material to prevent leakage of an internal material.

The polymeric compositions described herein may be used in an IOL, such as any of the fluid-driven IOLs described in U.S. Patent Application No. 60/433,046, filed Dec. 12, 2002, U.S. patent application Ser. No. 10/734,514, filed Dec. 12, 2003, U.S. patent application Ser. No. 10/971,598, filed Oct. 22, 2004, U.S. patent application Ser. No. 11/173,961, filed Jul. 1, 2005, U.S. patent application Ser. No. 11/252,916, filed Oct. 17, 2005, U.S. patent application Ser. No. 11/642,388, filed Dec. 19, 2006, and U.S. patent application Ser. No. 11/646,913, filed Dec. 27, 2006, the disclosures of which are hereby incorporated by reference in their entirety. The compositions may also, however, be used in a non fluid-driven IOL or a non-accommodating IOL.

A device implanted in the eye becomes exposed to the fluid in the eye. The fluid in the eye can, over time, diffuse through the device and have unintended and/or undesired effects on the physical characteristics of the device. For example, a polymeric IOL that is implanted in the eye may suffer from the diffusion of eye fluid into the IOL's polymeric material. Attempts have been made to coat ophthalmic devices with barrier layers to prevent such diffusion, but these procedures can be costly and time consuming. In addition, if an ophthalmic device contains a chamber or channel within the device which contains a fluid, there is a risk that that fluid can diffuse out of its fluid chamber and into the polymeric material. This results in a decrease in the amount of fluid that can be utilized by the IOL, as well as to possibly alter the physical characteristics of the polymeric material. Therefore, the inventive bulk polymers described herein can be used in ophthalmic devices to resist the diffusion of fluid into or out of the device.

For implantable devices that must be implanted through an incision in the sclera, it is generally desirable that the incision in the sclera be as small as possible while still being able to deform the device without damaging it. The device must also be able to reform to its initial configuration after delivery. The inventive polymers described herein can therefore be used in ophthalmic device that need to be deformed to be delivered through an incision, yet will return to their initial configuration once implanted in the eye.

Similarly, it may be desirable to increase the refractive index ("RI") of the ophthalmic device to increase its refractory power. An increase in the RI of the bulk polymer can allow the device to be thinner, yet maintain a desired power. This can also provide the device with a smaller delivery profile to reduce the size of the incision in the eye during implantation.

Improved properties of the polymers described herein include, without limitation, the modulus of elasticity, the index of refraction, the resistance to the diffusion of fluids, the responsiveness of the composition, mechanical strength, rigidity, wettability, and optical clarity. These properties are not necessarily mutually exclusive and the list is not intended to be exhaustive.

Some embodiments of the disclosure include a polymeric material for an ophthalmic device. The polymer comprises a first component, a second component, and a third or more components. In a preferred embodiment, the composition comprises butyl acrylate, trifluoroethyl methacrylate, phenylethyl acrylate, and a cross-linker such as ethylene glycol dimethacrylate. These monomers are not intended to be limiting and are provided by way of example.

To achieve the desired properties of the polymer described above, it is contemplated that particular monomers or other components may be selected to achieve specific properties, or that particular monomers and other components may be selected in combination to achieve specific properties.

Butyl acrylate, for example, a rubbery material, generally enhances the responsiveness of the polymeric material. Alternatives for butyl acrylate include alkyl acrylates and other monomers with suitable responsiveness properties. Alternatives for butyl acrylate which may demonstrate responsive properties include, without limitation, octyl acrylate, dodecyl methacrylate, n-hexyl acrylate, n-octyl methacrylate, n-butyl methacrylate, n-hexyl methacrylate, n-octyl methacrylate, 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate, and mixtures thereof. In addition, alternatives for butyl acrylate may include a branched chain alkyl ester, e.g. 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

In some embodiments butyl acrylate is present in the range from about 10% to about 80% by volume, and in some embodiments is present in the range from about 20% to about 70% by volume. In preferred embodiments butyl acrylate is present in the range from about 35% to about 65% by volume, and in more preferred embodiments from about 45% to about 65% by volume. All percentages recited herein are considered to be "by volume," unless specifically stated otherwise.

In some embodiments the polymer has a modulus of elasticity ranging from about 0.1 to about 0.6 Mpa. In some embodiments the modulus is between about 0.1 to about 0.3 Mpa.

Trifluoroethyl methacrylate, or suitable alternatives, can be added to the polymeric material to enhance the polymer's resistance to the diffusion of fluids as described herein. Generally, using a monomer with more fluorine atoms will enhance the polymer's resistance to the diffusion of fluid.

While the ethyl group of trifluoroethyl can potentially bind up to 5 fluorine atoms, a large number of fluorine atoms can reduce the refractive index of the polymer. In some embodiments, therefore, trifluoroethyl methacrylate will provide a desired balance between the polymer's resistance to diffusion and the polymer's refractive index.

Fluorocarbon monomers can enhance the polymer's resistance to the diffusion of fluid and some can be used as substitutes for trifluoroethyl methacrylate. Alternatives for trifluoroethyl methacrylate include fluoroacrylates and other monomers with that provide that polymer with suitable resistance to diffusion properties. Alternatives for trifluoroethyl methacrylate include, without limitation, heptadecafluorodecyl acrylate, heptadecafluorodecyl methacrylate, hexafluorobutyl acrylate, hexafluorobutyl methacrylate, tetrafluoropropyl methacrylate, octafluoropentyl acrylate, octafluoropentyl methacrylate, dodecafluoroheptyl methacrylate, heptafluorobutyl acrylate, trifluoroethyl acrylate, hexafluoro-iso-propyl methacrylate, pentafluorophenyl acrylate, and pentafluorophenyl methacrylate.

In some embodiments trifluoroethyl methacrylate is present in the range from about 5% to about 70%, and in some embodiments it is present in the range from about 10% to about 50%. In preferred embodiments it is present in the range of about 15% to about 30%, and in more preferred embodiments it is present in the range of about 18% to about 22%.

Phenylethyl acrylate, or suitable alternatives, can be included in the polymeric composition to increase the refractive index of the polymer. Phenyl groups in general can increase the refractive index of the polymer. Alternatives for Phenylethyl acrylate include phenyl acrylates and other monomers with that provide that polymer with suitably high refractive index.

Other groups which can be used to increase the refractive index of the polymer include, without limitation, benzyl (benzoyl), carbazole-9-yl, tribromophenyl, chlorophenyl, and pentabromophenyl. Exemplary monomers that can be used as alternatives to phenylethyl acrylate include, without limitation, tribromophenyl acrylate, 2-(9H-Carazole-9-yl) ethyl methacrylate, 3-chlorostyrene, 4-chlorophenyl acrylate, benzyl acrylate, benzyl methacrylate, benzyl methacrylamide, n-vinyl-2-pyrrolidone, n-vinylcarbazole, pentabromophenyl acrylate, and pentabromophenyl methacrylate, phenylethyl methacrylate, 2-phenylpropyl acrylate, or 2-phenylpropyl methacrylate.

In some embodiments phenylethyl acrylate is present in the range from about 5% to about 60%, while in some embodiments it is present in the range of about 10% to about 50%. In preferred embodiments it is present in the range of about 20% to about 40%, and in more preferred embodiments it is present in the range of about 26% to about 34%.

In some embodiments the polymer has a refractive index of between about 1.44 to about 1.52. In some embodiments the refractive index is between about 1.47 and about 1.52. In some embodiments the refractive index is between about 1.47 and about 1.5.

In some embodiments the composition also includes a cross-linking agent, such as ethylene glycol dimethacrylate. Examples of suitable crosslinking agents include but are not limited to diacrylates and dimethacrylates of triethylene glycol, butylene glycol, neopentyl glycol, ethylene glycol, hexane-1,6-diol and thio-diethylene glycol, trimethylolpropane triacrylate, N,N'-dihydroxyethylene bisacrylamide, diallyl phthalate, triallyl cyanurate, divinylbenzene; ethylene glycol divinyl ether, N,N'-methylene-bis-(meth)acrylamide, sulfonated divinylbenzene, divinylsulfone, ethylene glycol diacrylate, 1,3-butanediol dimethacrylate, 1,6 hexanediol diacrylate, tetraethylene glycol dimethacrylate, trifunctional acrylates, trifunctional methacrylates, tetrafunctional acrylates, tetrafunctional methacrylates and mixtures thereof.

Cross-linking agents may be present in amounts less than about 10%, less than about 5%, less than about 2%, or less than about 1%. The cross-linking agent(s) can cause the polymers to become interlaced within a tri-dimensional space, providing for a compact molecular structure having an improved elastic memory, or responsiveness, over the non-crosslinked composition.

In some embodiments, the polymeric compositions also includes one or more ultraviolet (UV) light absorbing materials, such as an acrylate or methacrylate functionalized benzotriazole or benzophenone, in amounts less about 5%. In some embodiments the UV light absorbing material(s) is present in the range from about 0.05% to about 2%. Suitable ultraviolet light absorbers for use can include, without limitation, β-(4-benzotriazoyl-3-hydroxyphenoxy)ethyl acrylate, 4-(2-acryloyloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryloyloxyethylphenyl)-2H-benzotriazole, 2-[3'-tert-butyl-2'-hydroxy-5'-(3"-methacryloyloxypropyl)phenyl]-5-chloro-benzotriazole, 2-[3'-tert-butyl-5'-(3"-dimethylvinylsilylpropoxy)-2'-hydroxyphenyl]-5-m-ethoxybenzotriazole, 2-(3'-allyl-2'-hydroxy-5'-methylphenyl)benzotriazole, 2-[3'-tert-butyl-2'-hydroxy-5-(3"-methacryloyloxypropoxy)phenyl]-5-chloro-benzotriazole and 2-[3'-tert-butyl-2'-hydroxy-5'-(3"-methacyloyloxypropoxy)phenyl]-5-chloro-benzotriazole.

One skilled in the art will appreciate that different other chemistries of UV light absorbants may be selected.

One or more suitable free radical thermal polymerization initiators may be added to the polymeric compositions described herein. Examples of such initiators include but are not limited to organic peroxides, such as acetyl peroxide, lauroyl peroxide, decanoyl peroxide, stearoyl peroxide, benzoyl peroxide tert-butyl peroxypivalate, peroxydicarbonate, and the like. Such an initiator can be added in the range of about 0.01% to about 1% of the total polymer mixture.

Alternative UV initiators include those known in the field such as, for example but not limited to, benzoin methyl ether, benzoin ethyl ether, Darocur® 1173, 1164, 2273, 1116, 2959, 3331 (EM Industries) and Irgacur® 651 and 184 (Ciba-Geigy, Basel, Switzerland).

The diffusion resistant properties of the inventive polymers described herein may be further enhanced by providing a barrier layer on the exterior surface of the ophthalmic device. In addition, if the device comprises a fluid chamber disposed within the device (such as a fluid chamber disposed in a fluid-driven accommodating IOL), the device can also have a barrier layer on the inner surface of the fluid chamber to increase the resistance to diffusing out of the fluid chamber. The barrier layer can be a thin layer of a fluorocarbon materials or polymers, examples of which include hexafluoroethane, hexafluoropropylene, hexafluoropropane, octofluoropropane, polytetrafluoroethylene, and 1H, 1H, 2H-perfluoro-1-dodecene. The barrier layer can be deposited or covalently bonded on the solid surfaces of the ophthalmic device, either individually or in combination through a variety of manufacturing processes. One common manufacturing process is plasma deposition.

The layers formed by plasma deposition will generally be very thin, for example, from about 20 to about 100 nanometers. Because fluorocarbon polymers generally have low refraction indices, a barrier layer with a thickness that is less than a quarter of the wavelength of visible light will not be seen with the naked eye.

As stated above, the inventive polymers described herein may be used in an IOL with fluid disposed therein, such as in fluid chambers. In general, the viscosity of a fluid is related to the diffusion properties of the fluid; a low viscosity fluid can more easily diffuse through the polymer.

An ophthalmic device may contain silicone oil. The amount of silicone oil that diffuses through the polymer can be reduced by selecting a silicone oil with narrow molecular weight distribution, in particular with the removal of low molecular weight silicone oil molecules. A sequence of stripping processes is commonly used to remove low molecular weight components in silicone oil. In general, low molecular weight components will diffuse faster than higher molecular components. However, higher molecular weight components contribute to an increase in the viscosity which requires a greater force to drive the fluid throughout the IOL. Therefore, silicone oil with a narrow molecular weight distribution is preferred. The fluid disposed within the ophthalmic device is not limited to silicone oil and can be, for example, a saline solution.

In some embodiments, however, the IOL components are substantially index matched, such that the deflection of one of the surfaces of the IOL contributes significantly to any change in power during accommodation. For example, the bulk polymer will be substantially indexed matched to any fluid within the IOL. Substantially index-matched, as that phrase is used herein, include minimal differences in refractive indexes between components of the IOL. For example, if adhesives are used in the manufacturing of an IOL, those adhesives may have different refractive indexes but those differences will be negligible when considering the overall power changes of the accommodating IOL.

In some embodiments the TG of the polymer is about −20° C., and can stretch to about 4× the length without breaking.

The optics portion and the haptic portion(s) may be comprised of the same polymeric composition or may be comprised of different compositions. The composition of the optics and haptic(s) portions may depend on which properties are desired in each of the components. For example, it may not be necessary to achieve a high refractive index in the haptics portion as the haptics do not generally contribute to the focusing of light, and thus a polymer used for the haptics may not need a high refractive index. Similarly, for example, it may be desirable for the haptics portion to possess different responsiveness properties than the static optics portion.

The following non-limiting examples illustrate certain aspects of the present disclosure.

Example 1

The following formulation is added together and mixed well:

|  | Quantity | % Quantity |
|---|---|---|
| Trifluoroethyl methacrylate | 4 ml | 19.6% |
| Butyl acrylate | 10 ml | 49.0% |
| Phenyl ethyl acrylate | 6 ml | 29.4% |
| Ethylene glycol dimethacrylate | .2 ml | .980% |
| Darocur 1173 (UV initiator) | .2 ml | .980% |

The polymer can be manufactured by pour the formulation into a mold and curing the polymer, with either UV or thermal curing. The resulting polymer had a swell fraction of 0 in silicone oil, a refractive index of 1.477, and a modulus of elasticity of 0.163 Mpa.

Example 2

The following formulation can be added together, mixed well, and processed the same as the formulation in Example 1:

|  | Quantity | % Quantity |
|---|---|---|
| Trifluoroethyl methacrylate | 4 ml | 19.5% |
| Butyl acrylate | 12 ml | 58.5% |
| Phenyl ethyl acrylate | 4 ml | 19.5% |
| Ethylene glycol dimethacrylate | .3 ml | 1.46% |
| Darocur 1173 (UV initiator) | .2 ml | .976% |

The resulting polymer had a swell fraction of 0.019, a refractive index of 1.473, and a modulus of elasticity of 0.27 Mpa.

While the embodiments above provided exemplary polymeric formulations, additional exemplary formulations are provided below that have higher refractive indices that those above. Increasing the refractive index may be desirable to increase the base power of the intraocular lens. In some embodiments, the refractive index of the polymeric material of the intraocular lens is between approximately 1.48 and approximately 1.53, optionally between 1.50 and 1.53. The refractive index of the bulk polymer may be increased by increasing the concentration of phenylethyl acrylate as a percentage of weight of the polymer. Other components can be modified to compensate for increased concentrations of the monomer comprising a phenyl group. Table 1 below illustrates additional exemplary polymeric formulations for use in ophthalmic devices and their components, wherein the refractive index is higher than some embodiments above. The first three formulations have refractive index values very close to 1.5180 at 532 nm and 35 C, which is an example of a RI between 1.50 and 1.53. The fourth formulation is similar to some examples provided above. All four formulations in Table 1 include BA, PEA, and TFEMA.

An exemplary significant advantage of the illustrative formulations in Table 1 (including the relatively higher refractive index) is that they show dramatically lower propensity to swell when exposed to silicone fluids that are commonly used in some fluid-driven accommodating intraocular lenses, such as those incorporated by reference herein. Data supports the reduced swelling, and the reduced swelling manifests as significantly improved power stability, and potential ability to conduct accelerated aging studies without swelling-induced power drops seen in some fluid-driven accommodating intraocular lenses.

TABLE 1

| | | Components | | | | | | |
|---|---|---|---|---|---|---|---|---|
| Formulation | | BA | PEA | TFEMA | EGDMA | UV Blocker | Perkadox | Total |
| 1 | wt. % | 6.60 | 67.12 | 25.05 | 1.00 | 0.10 | 0.13 | 100.00 |
| 2 | wt. % | 14.24 | 65.52 | 19.01 | 1.00 | 0.10 | 0.13 | 100.00 |
| 3 | wt. % | 12.05 | 65.71 | 21.02 | 1.00 | 0.10 | 0.13 | 100.00 |
| 4 | wt. % | 44.48 | 30.89 | 23.38 | 1.03 | 0.10 | 0.13 | 100.00 |

Formulations 1-3 in Table 1 can be used in, for example, an optic portion of an accommodating intraocular lens ("AIOL"), wherein the accommodating intraocular lens is a fluid-driven, or a peripheral portion of an AIOL.

The specific monomers provided herein are provided merely as an example, and the scope of the disclosure is not so limited. For example, in some embodiments the percentage of BA is between 2 and 20%, such as between 3 and 17%. In some embodiments the percentage of PEA is between 50 and 80%, such as between 60 and 75%. In some embodiments the percentage of TFEMA is between 10 and 35%, such as between 15 and 30%.

The first three formulations in Table 3 are also examples of polymeric materials that comprise an alkyl acrylate present in the amount from 3% to 20%, a fluoroacrylate present in the amount from 10% to 35%, and a phenyl acrylate present in the amount from 50% to 80%.

Figure 3:
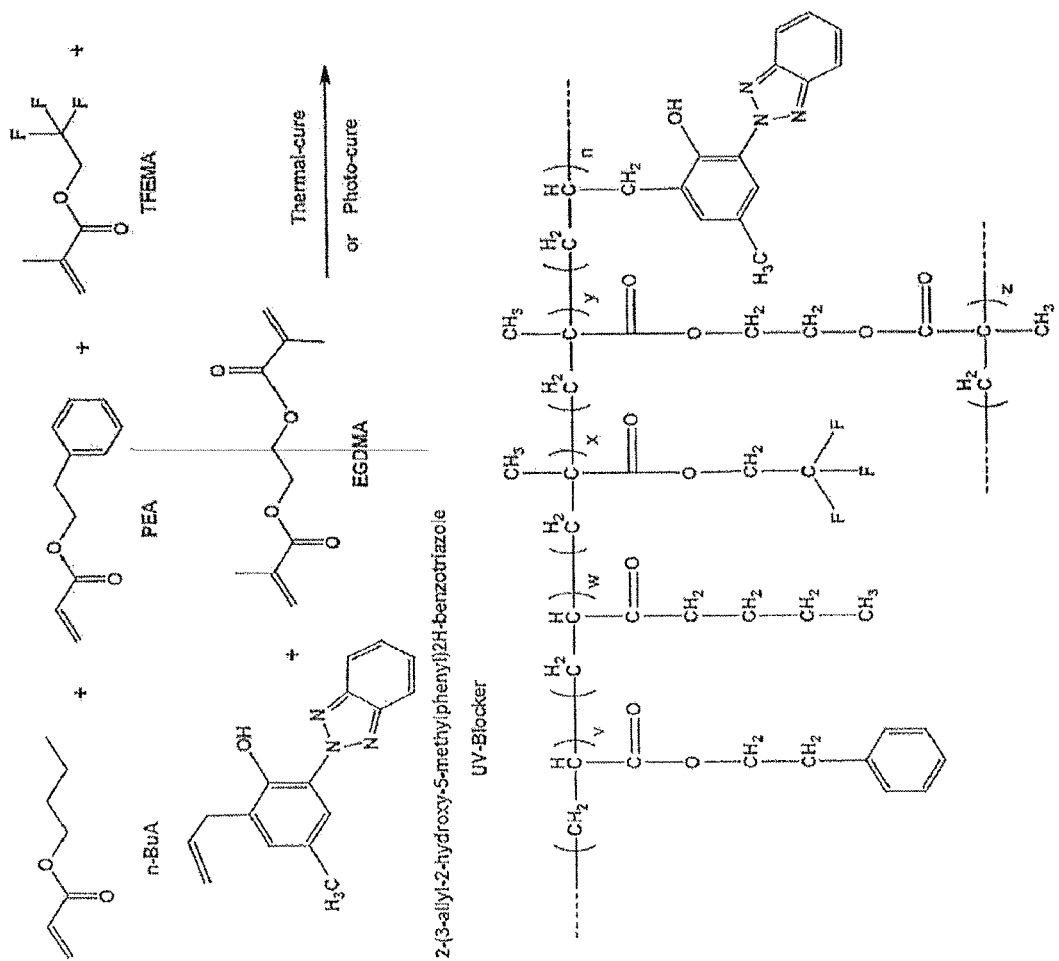
FIG. 3 illustrates a curing process.

The polymeric materials can be manufactured, including curing, using a variety of manufacturing steps. FIG. 3 illustrate an exemplary process of curing three monomers (i.e., BA, PEA, and TFEMA), a UV blocker, and a cross-linker such as EGDMA, resulting in a cured polymeric material that includes the three monomers. Any of the polymeric materials can be manufactured in this manner.

Figure 4:
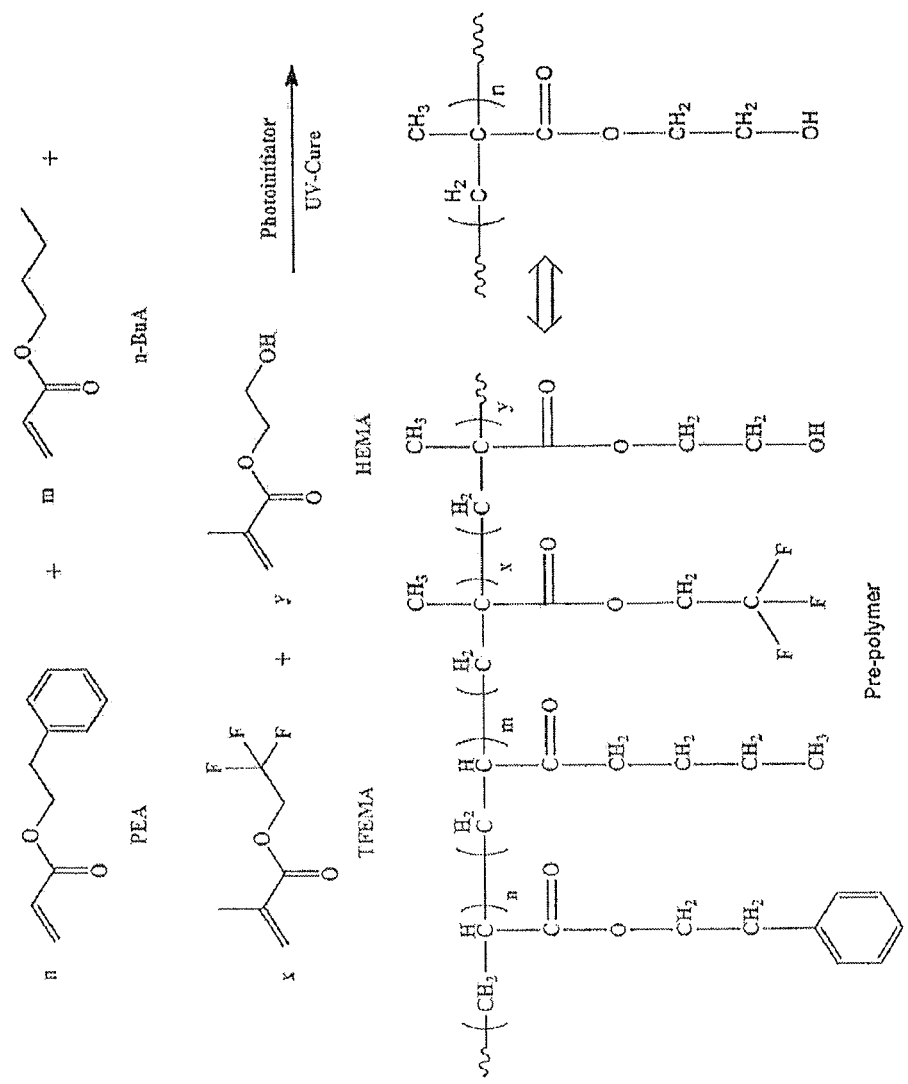
FIG. 4 illustrates the synthesis of a pre-polymer.
Figure 6B:
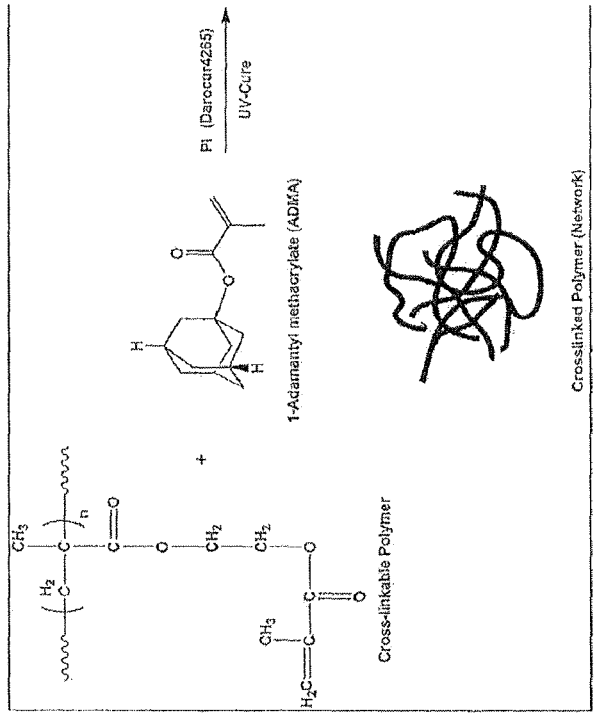
FIGS. 6A and 6B show crosslinked polymer formation and exemplary adhesive design.
Figure 6A:
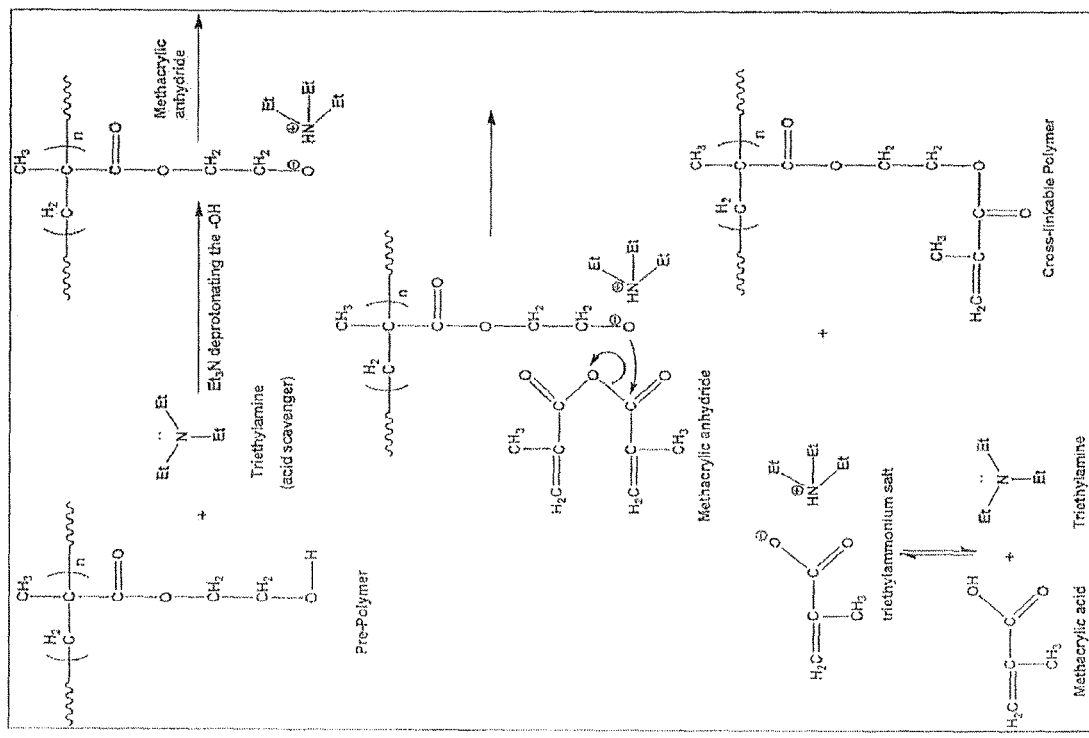

FIG. 4 illustrates an alternative manufacturing process, wherein pre-polymers are first created with a plurality of monomers (in this example they are the same as in FIG. 3, but need not be), wherein the pre-polymers are not yet cross-linked (not yet fully cured), as is shown in FIG. 4. The monomers are first combined with a monomer that includes a hydroxyl moiety, which is subsequently converted to a crosslinkable methacrylate, which allows the cross-linkable polymer to be fully cured. In some embodiments the monomer that includes the hydroxyl moiety is a methacrylate (e.g., hydroxyethyl methacrylate ("HEMA")) or an acrylate (e.g., hydroxyethyl acrylate ("HEA"), hydroxybutyl acrylate ("HBA")). In the exemplary FIG. 4 HEMA is used FIG. 6A illustrates an exemplary process of making a cross-linkable polymer from a pre-polymer (such as the pre-polymer in FIG. 4), in which the hydroxyl moiety is converted into a methacrylate (bottom right in FIG. 6A), which can then be crosslinked to form a cured polymeric material, which can be used to make any of the components of any exemplary IOL herein.

As is described in more detail with respect to the discussion on adhesives (which is fully incorporated into this section of the disclosure), the cross-linkable polymers, such as those described above, can be combined with a hydrophilic reactive diluent. Use of a hydrophilic monomers (e.g., HEMA, HBA) as a reactive diluent for cross-linkable polymer will, upon cure, give interpenetrating networks in the polymeric matrix with a hydrophilic homopolymer as the second phase. Long homopolymer "blocks" can increase efficacy of hydrophilic components relative functionality in random copolymers. In some embodiments the polymer is developed by using about 25-35% (e.g., 30%) HEMA or HBA as a reactive diluent for the cross-linkable polymer. In some exemplary methods of manufacture, no phase separation occurred upon curing and the cured polymeric material was clear. These cross linkable polymer-based formulations are well suited for high precision (very low shrinkage) production of directly molded parts, such as with haptics and optic portions or any of the accommodating intraocular lenses described or incorporated by reference herein.

An additionally exemplary advantage of incorporating one or more hydrophilic monomers (e.g., HEMA, HBA) into the polymeric material as the reactive diluent is that it can reduce water-induced haze or glistenings (i.e., water vacuoles in the material).

Figure 5A:
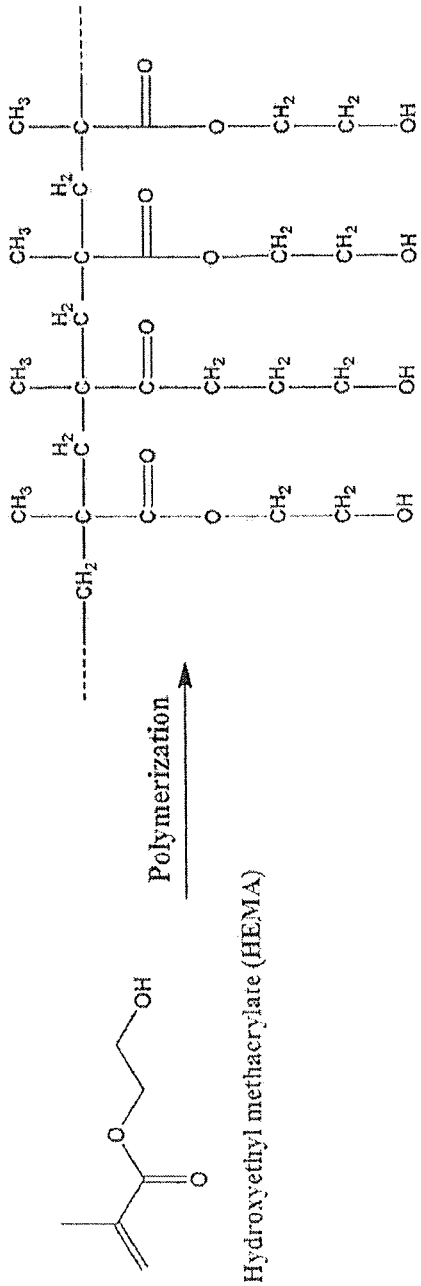
FIGS. 5A and 5B illustrate exemplary hydrophilic materials.
Figure 5B:
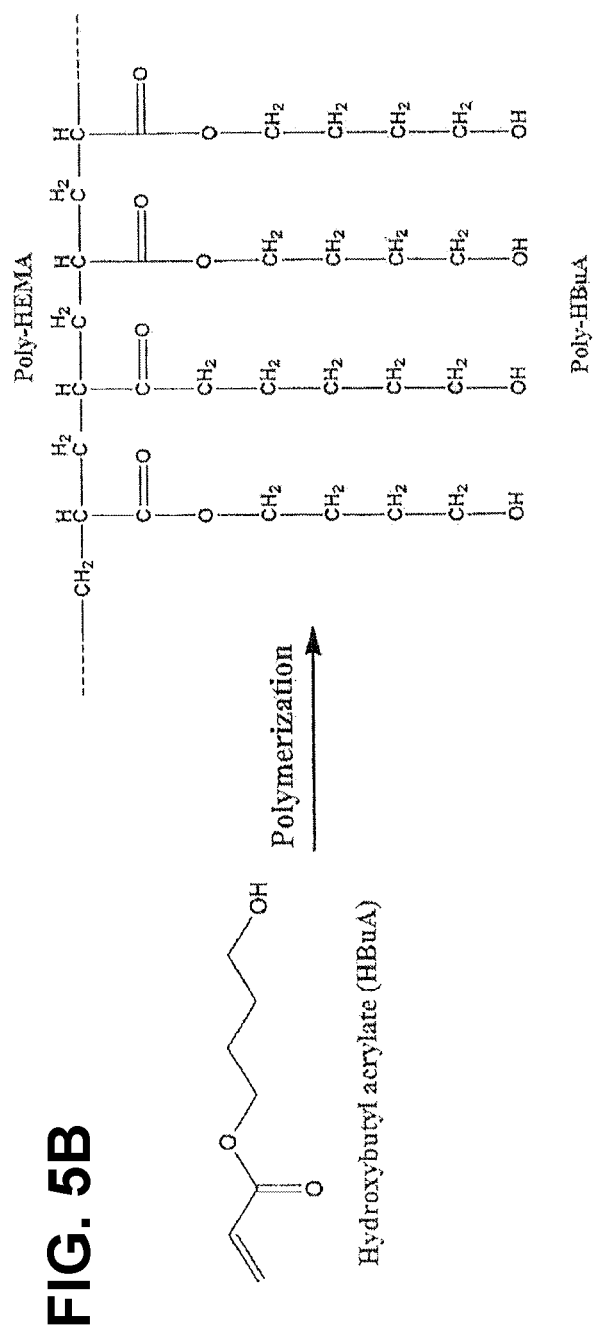

FIGS. 5A and 5B illustrates the polymerization of exemplary hydrophilic materials, with HEMA being shown in FIG. 5A, and FIG. 5B showing HBA.

Adhesives

One aspect of this disclosure describes adhesives that can be used to bond first and second polymers together, optionally first and second polymers in an intraocular lens. While the disclosure describes the adhesives and polymers for use in ophthalmic applications, it is not intended to be so limited. The materials described herein can be used in other suitable applications. The exemplary polymeric materials described above (e.g., example 1, example, 2, and Table 1) are merely examples of formulation of polymers for the first and second components that are bonded together. The adhesives described herein will be described in reference to polymers described herein, but the concepts herein can be applied to other polymeric materials and other adhesives. The examples provided herein are merely exemplary and the disclosure is not intended to be limited to the specific adhesives or the specific polymers herein.

During the manufacture of some ophthalmic devices, two or more polymeric bodies are adhered, or glued, together. The bond(s) should be strong enough so that the two or more bodies remain adhered together during use and during the implantation procedure. For example, the bonds must hold even if the device needs to be reconfigured or deformed during loading and/or delivery into the eye. Additionally, the presence of the adhesive should not cause the optical clarity of the device, such as at or near the bond, to decrease to an unacceptable level. The adhesive and polymer combinations herein improve or maintain the mechanical integrity of the adhesive/polymer bond, as well as maintain an acceptable level of optical clarity.

One aspect of the disclosure is an adhesive that has a first component that is the same or substantially the same material, or has substantially similar properties, as first and second polymeric bodies that are adhered together. The first and second bodies alternatively can have different formulations. As used herein, the adhesives are used to adhere a "first body" to a "second body."

In some embodiments the first and second bodies are first cured, then adhered together using adhesion techniques herein.

In some embodiments the adhesive includes first and second primary components and a curative additive (e.g, a photoinitiator). In a purely exemplary embodiment that includes an exemplary method of manufacturing, the first primary component (e.g., about 50-75%) is a crosslinkable polymer ("CLP"; the discussion above on cross-linkable polymers is incorporated into this aspect of the disclosure) that has the same, or similar composition as, or substantially similar properties as, the first and second bodies. Because the CLP is not yet cross-linked, it behaves as a flowable, dissolvable, thermoplastic material, rather than a thermoset material. The CLP is then compounded with a second primary component, a reactive acrylic monomer diluent (such as ADMA, shown in FIG. 16, e.g., about 20-50%), and the remaining constituents are about 2% photoinitiators for curing the glue. In the bond line between the first and second bodies, the CLP is too big/bulky to be able to migrate into either body, whereas the reactive acrylic monomer diluent and photoinitiators can migrate/diffuse across the bond line and into both cured polymeric bodies. Depending on the time, temperature, and thickness of the bond line, the reactive acrylic monomer diluent and initiators diffuse to a certain (controllable) extent and are subsequently cured (e.g., by UV light), creating an interpenetrating network of reactive acrylic monomer diluent (e.g., ADMA) in the first and second bodies, as well as a now crosslinked polymer (that is the same as or similar to, or has similar properties to the first and second bodies) also with a permeating reactive acrylic monomer diluent network. If the extent of diffusion is such that the reactive acrylic monomer diluent concentration is essentially equal across and within the bond line, then properties of the materials across the region will be substantially the same.

In some embodiments the first primary component (that optionally has the same or similar composition as the first and/or second bodies) is about 55% to about 80% (such as about 55% to about 75%) of the adhesive. In some embodiments the second primary component (reactive acrylic monomer diluent) is about 18% to about 43% (such as about 23% to about 43%) of the adhesive.

The adhesives herein provide some mechanical advantages. In general, the bond strength is better over time, which increases the life expectancy of the device. When using substantially the same materials, or materials with substantially similar properties, an interpenetrating network of materials is formed between the polymer and the adhesive where the resulting bonded material is substantially the same throughout. Additionally, the mechanical and thermal properties of the materials can be substantially the same as well. For example, the modulus of elasticity of the polymer and adhesive can be designed to be the same or substantially the same. Additionally, the surfaces energies can be substantially the same, which can help keep ambient water out of the bond and prevent it from migrating into the device and forming water droplets.

Additionally, when using a first component of the adhesive that is the same or substantially the same as a first body material, it is possible to better control the cross-linking during manufacture, which leads to less shrinkage when the bond is cured. Shrinkage invariably occurs when monomers are cured (typically about 10% by volume for most acrylic monomers), but the crosslinking of the CLP occurs with almost no shrinkage since this can be considered as the final about 1% of the cure of the essentially all pre-cured material, thus the more CLP that is used in the adhesive formulation, the less shrinkage that that formulation will exhibit upon cure. Moreover, the diffusion of, for example, ADMA into the acrylic adhered ensues with concomitant swelling that may offset some or all of the cure-induced shrinkage.

In one aspect of the disclosure, the term "substantially the same" is intended to include compositions that have the same components in nearly the same amount, or similar components, or properties that substantially the same. In some embodiments, the term substantially the same may refer to compositions that include the same components and have percentage of each component that is within 1-50% of the components by either weight or volume of the composition it is being compared to. In other embodiment, substantially the same may be used to refer to compositions having substantially the same physical characteristics (e.g. viscosity, refractive index, structure, etc.).

Additionally, there are optical advantages in using an adhesive material with a first component that is the same or substantially the same as the polymeric body material. As set forth above, the surface energies can be substantially the same, and there are substantially no hydrophobic sites. Substantially the same surface energy prevents water droplets from forming, which prevents the optical clarity from decreasing. Additionally, by using substantially the same material, the refractive index of the adhesive and the bonded polymers can be substantially the same. While a difference in refractive index between an adhesive and polymer may not create any noticeable optical disturbances, creating the materials with substantially the same refractive index can reduce the likelihood of such disturbances.

The cross-linkable polymer of the adhesive need not have the same formulation (same monomers and same percentages), or even the same monomers, as the polymeric formulation as the first and/or second polymeric bodies being bonded together. It is advantageous that the cross-linkable polymer formulation have similar properties to the formulation of the first and/or second polymeric bodies, which are described above, but in other embodiments the can be quite different. By way of example only, formulation #4 from Table has been used as a crosslinkable polymer in an adhesive formulation, and has been used to adhere polymeric bodies that have formulations as set forth in any of formulations #1-#3 in Table 1. In this example the adhesive cross linkable polymer and polymeric formulation for the first and second bodies both include three monomers that are the same, but at different percentages. This is an example of being the substantially the same or having substantially similar properties. The bond strength in this example was very strong. In some embodiments the adhesive cross linkable polymer and polymeric formulation for the first and second bodies can be the same.

Any intraocular lens that includes first and second components being bonded together can be adhered together using concepts herein.

In some embodiments the adhesive is formed according to the method shown in FIG. 16 above to form a cross-linkable polymer. That is, a pre-polymer is used to create cross-linkable polymers, which when mixed with the reactive diluent (e.g. ADMA) can be cured, with the first and second bodies, to form a crosslinked polymer.

The disclosure herein also describes exemplary fluids that can be used in intraocular lenses. In some embodiments the fluids are silicone oils, and in some embodiments the intraocular lenses are accommodating intraocular lenses.

An ophthalmic device may contain one or more silicone oils. Silicon oil may be used in accommodating intraocular lens that uses fluid movement to effect optical power change in the IOL. Silicon oil may also be used in non-accommodating intraocular lenses as well. When silicone oil is used in accommodating IOL with a bulk material such as a polymeric material, some of the oil components can pass into the bulk material, causing the bulk material to swell. The selected silicone oil or oils therefore avoids the undesirable swelling of the bulk polymer. Exemplary polymeric materials that can be used for the bulk material of the IOL can be found herein.

The amount of silicone oil that diffuses through the polymer can be reduced by selecting a silicone oil with narrow molecular weight distribution, in particular with the removal of low molecular weight silicone oil molecules. A sequence of stripping processes can be used to remove low molecular weight components in silicone oil. In general, low molecular weight components will diffuse faster than higher molecular components. However, higher molecular weight components contribute to an increase in the viscosity which requires a greater force to drive the fluid throughout the IOL. Therefore, silicone oil with a narrow molecular weight distribution is preferred. The fluid disposed within the ophthalmic device is not limited to silicone oil and can be, for example, a saline solution.

One characteristic of silicone oil that helps ensure an adequate response and avoids undesirable swelling is the polydispersity index ("PDI") of the silicone oil to be used in the IOL. PDI is generally a measure of the distribution of molecular mass in a given sample. A relatively low PDI indicates a relatively narrow range of molecular weights. The silicone oils described herein have a PDI less than about 1.5, and more particularly less than or equal to about 1.3. In other instances, the PDI of the silicon oils is less than about 1.2

A second characteristic of the silicone oil that helps ensure an adequate response and avoids undesirable swelling is the mean molecular weight of the silicone oil. When high concentrations of relatively low molecular weight components are present in the silicone oil, a greater number of low molecular weight components pass into the bulk material of the IOL causing the swelling of the bulk material. To avoid undesirable swelling, the concentration of relatively low molecular weight components should be minimized. By reducing the concentration of relatively low molecular weight components and maintaining a high concentration of relatively high molecular weight components, fewer low molecular weight components will pass into the bulk polymer material, reducing the amount of swelling that occurs in the bulk material.

The PDI of the silicone oil and the mean molecular weight of the oil are related—by lowering the PDI of the silicone oil while providing silicone oil with high concentrations of relatively high molecular weight components and low concentrations of low molecular weight components, the response of the IOL is maintained (by providing a silicone oil with suitable viscosity) and undesirable swelling is avoided. Additionally, providing silicone oil with a low PDI and very low concentrations of small molecular weight components means that the silicone oil has a molecular weight just large enough to avoid swelling of the polymer.

In some embodiments silicone oil is provided that has a mean molecular weight between about 4500 and about 6500 Daltons, or having a mean molecular weight of about 5000 and about 6500 Daltons. Silicon oils having molecular weights within this range are large enough to substantially avoid swelling of the bulk polymeric material. This is preferable to the alternative, which is using a higher molecular weight silicone oil which has inherently fewer small molecule components because almost all molecules comprising it are large. High molecular weight silicone oils can have a correspondingly high viscosity, which can reduce the response time of the accommodating IOL.

The silicone oils described herein have a very low concentration of relatively low molecular weight components. The very low molecular weight components are present in an amount less than about 200 ppm of each component, and in some embodiments less than about 100 ppm. In some particular embodiments the very low molecular weight components are present in an amount less than about 50 ppm.

The relatively low molecular weight components include those less than or equal to about 1000 Daltons. For example, in some embodiments the concentration of components less than or equal to about 1000 Daltons is not more than about 50 ppm.

In one particular embodiment, silicone oil is provided in which no more than 20% of the total silicone by weight is comprised of components below about 4000 Daltons; no more than 10% of the total polymer fluid by weight is comprised of components below 3000 Daltons; and no more than 50 ppm of any components below 1000 Daltons.

The estimated molecular weights and polydispersities described herein are relative to polystyrene molecular weights standards.

The silicone oil generally needs to be designed in such a way as to avoid adverse interactions with the surrounding bulk IOL material, such as swelling, fogging, dissolving or reacting with the material (e.g., poly acrylate) in some IOLs. The degree of solubility of the silicone oil in the bulk material is dependent on the chemical structure and molecular weight distribution of the silicone oil. Other parameters that influence this interaction are the composition and properties of the bulk material such as homogeneity, chemical structure, hydrophobicity, modulus, and crosslink density.

The viscosity of the silicone oil also generally needs to be defined and minimized because, in embodiments in which the fluid-driven accommodating IOL operates dynamically, the IOL must have an appropriate response time. In some embodiments, the viscosity of the silicone oil is no more than 2400 cP.

In some embodiments the silicone oil is made from a cyclotrisiloxane comprising a ratio of two dimethyl siloxane units to one diphenyl siloxane unit. In some embodiments the oil is at least 95% (e.g., 100%) of a single cyclotrisiloxane comprising a ratio of two dimethyl siloxane units to one diphenyl siloxane unit.

In some embodiments the oil is a diphenyl siloxane and dimethyl siloxane copolymer with about 20% diphenyl siloxane and about 80% dimethyl siloxane.

In some embodiments, the silicon oil may be a single component of diphenyl siloxane (e.g. approximately 100%). In other embodiments, the percentage of diphenyl siloxane is approximately 95% or more. In these embodiments the refractive index of the silicone oil is about 1.5180, which is an example of between 1.50 and 1.53. In some embodiments a silicone oil that is approximately 100% diphenyl siloxane can be used in an accommodating intraocular lens that has formulations such as #1-#3 in Table above. In these embodiments the fluid and polymer were index matched to about 1.518.

In some embodiments, the diphenyl siloxane polymeric compound has a mean molecular weight of between approximately 4500 and approximately 6500 Daltons.

In some IOLs it may be desirable to avoid creating an optical interface between the bulk material of the IOL and the silicone oil within the IOL. This can be done by index-matching the silicone oil to the bulk material of the IOL, which in some embodiments is a polymeric material. "Index-matching" as used herein refers to minimizing the optical interface between first and second media. For example, index-matching silicone oil and a polymeric material refers to attempting to eliminate an optical interface there between, and "substantially the same" refers to indexes of refraction that, even though they may be slightly different, are intended to be as close as possible to minimize the difference in refractive indexes.

In some embodiments in which the silicone oil is index-matched to the bulk polymeric material, the refractive index of silicone oil is between about 1.47 and about 1.55, and in some embodiments is between about 1.50 and about 1.53.

In some embodiments the silicone oil must be able to be filtered through an about 0.7 micron filter. In some embodiments the percent volatiles are less than about 0.2%. In some embodiments the silicone oil has a chromatic dispersion less than or equal to about 0.035 refractive index units in the visible range of 400 nm to 750 nm at 35° C. In some embodiments the silicone oil components are fully miscible with each other without evidence of phase separation (i.e.

cloudiness or suspensions). In some embodiments the silicone oil has greater than 85% transmittance in the range of 400 nm to 1100 nm for about a 1 cm thick fluid sample.

In addition, the silicone oil should be clear, colorless, have less than about 10 ppm heavy metals and other insoluble inorganics contaminants, and have substantially no silanols.

Synthesis of Silicone Oils

The molecular weight, polydispersity, and in some instances the refractive index of the silicone oil can be controlled by the way in which the silicone oil is synthesized and purified. The viscosity of the oil is related to the molecular weight of the oil, the polydispersity of the oil, and the architecture of the bulk polymer, all of which are influenced by the synthesis and purification of the polymer. However, a target viscosity cannot be arbitrarily selected independent of the target molecular weight, polydispersity, composition, and architecture of the silicone oil. A general class of polymer synthesis reactions known as "living polymerization reactions" can offer the degree of control necessary to assist in meeting some of the design requirements for a silicone oil.

The term "living polymerization" implies a polymerization reaction that does not have a significant number of chain terminating or chain transferring side reactions. The absence of side reactions allows living polymerizations to be used to synthesize a variety of materials that would be otherwise difficult to prepare. This class of polymerization reactions can be used to prepare polymers with a variety of 1) architectures—including linear, "star", and "comb" polymers; 2) compositions—homopolymers, random copolymers, block copolymers, and graft copolymers; and 3) functionalized polymers—one and two end functional polymers, and side functional polymers. This class of polymerization reactions can be used to prepare polymers that often have a narrow molecular weight distribution and at a variety of molecular weights. As a result, living polymerizations are often employed when polymers with specific structures and compositions are needed. For example, a polymer with a large molecular weight distribution can be considered to be a mixture of a large number of compounds, and the properties of the material are some function of that distribution. Polymers that have a small molecular weight distribution, however, as can result from a living polymerization, can be considered a "purer" sample, with properties that are better defined.

Anionic and cationic living polymerizations have been described in the art. More recently, radical living polymerizations may have been developed. In an example of an anionic synthetic route, the use of alkyl lithium compounds in the ring opening polymerization of cyclotrisiloxanes appears to be a "living" polymerization, allowing for the degree of control needed to make the silicone oils described above. By varying the ratio of phenyl containing cyclotrisiloxanes to methyl only containing cyclotrisiloxanes (that is, preparing a random block copolymer), the refractive index of the silicone oil can be varied between the refractive index of either pure homopolymer alone (i.e., between pure diphenyl polysiloxane and pure dimethyl polysiloxane).

As another example, the refractive index of the silicone oil composition can be varied by varying the ratio of a tetramethyl-diphenyl-cyclotrisiloxane to hexamethyl cyclotrisiloxanes. Varying this ratio can provide different refractive indexes between about 1.40 and about 1.54, including those between about 1.47 and 1.49.

As mentioned above, a living polymerization also offers the advantage of being able to prepare polymer products of a targeted molecular weight. This can be accomplished by varying the monomer to initiator ratio during the polymerization reaction, an application which can be applied to the preparation of silicone oils of a specified formula weight.

The feature of a narrow range of molecular weight products is also an advantage that can be realized in the preparation of silicone oils because fewer low molecular weight oligomers are made during the polymerization reaction. The smaller quantity of the low molecular weight materials prepared minimizes the amount of purification that needs to occur later to remove them from the higher molecular weight products. For example, when fewer low molecular weight oligomers are made during the polymerization reaction, it is easier to extract the low molecular weight materials when purifying the synthesized silicone oil using a supercritical $CO_2$ extraction (described below), resulting in higher yields of the desired product.

While the viscosity of a polymer is not directly related to the way in which the polymer is prepared, a living polymerization can also be used to indirectly modify this feature of the product polymer. Living polymerizations can be used to make polymer architectures that would be difficult to accomplish using other synthetic strategies. For example, "comb" polymers, "star" polymers, and other branched structures can be prepared, which, even though they have a very similar chemical composition to a "linear" polymer, may have different physical properties (e.g., viscosity), because of the different physical geometries those structures have. Preparation of a highly branched silicone oil may yield a product which has a significantly lower viscosity than a silicone oil with the same molecular weight but a linear structure.

Silicone oils can also be prepared using other synthetic strategies such as the base catalyzed ring opening of cyclotrisiloxanes, and the condensation of dialkyldichloro silanes with water. These synthetic strategies can also prepare silicone oils with many of the characteristics described above, but can require more effort on purification.

Purification of Silicone Oils

Silicone oils can be purified in a variety of ways. The silicone oils obtained after a polymerization reaction as discussed above, may contain silicon oil polymer variants having different molecular weights. Low molecular weight silicone oils may cause undesirable swelling of the bulk polymeric material and should be minimized. Wiped film evaporation can be used to remove low molecular weight compounds that have a high boiling point. The silicone oil product may, however, be discolored on excessive heating when using wiped film evaporation.

Supercritical $CO_2$ extraction is one exemplary purification method that can be used to selectively remove fractions of silicone oil based on molecular weight and based on chemical affinity. Supercritical $CO_2$ extraction to purify silicone oils to produce silicone vitreoretinal tamponades is described in U.S. Pat. No. 7,276,619, the entire disclosure of which is incorporated by reference herein. These oils are not used for IOLs, are particularly not in fluid-drive accommodating IOLs. Pressure, temperature, rate of extraction conditions, and the use of co-eluting solvents such as, for example, acetone, can be varied to yield fractions that have a narrow molecular weight distribution (i.e., a low PDI). A mixture can be separated in such a way as to strip the very low and very high molecular fractions from a sample achieving the desired molecular weight. Because supercritical extraction conditions can be varied to get separation based on chemical affinity, this purification method can also be used to achieve a desired refractive index. Supercritical $CO_2$ extraction can therefore be used to produce a silicone oil with, for example, an index of refraction substantially the same as a bulk polymer to be used in an intraocular lens (e.g., in a fluid-driven accommodating intraocular lens).

Tables 2-4 provide data from exemplary supercritical $CO_2$ extractions of sample silicone oils.

TABLE 2

| Silicone Oil Sample | Time at 85 C. (Hrs) | % Weight Change |
|---|---|---|
| 1 | 404 | 43.15 |
| 2 | 404 | 24.48 |
| 3 | 404 | 11.11 |
| 4 | 404 | 6.15 |
| 6 | 404 | 1.67 |
| 7 | 404 | 13.25 |

TABLE 3

| Silicone Oil Sample | Mean RI |
|---|---|
| 1 | 1.477792 |
| 2 | 1.48604 |
| 3 | 1.487633 |
| 4 | 1.49067 |
| 5 | 1.494362 |
| 6 | 1.498737 |
| 7 | 1.492858 |

TABLE 4

| Silicone Oil Sample | Viscosity (cP) at 25.0 C. | stdev |
|---|---|---|
| 1 | 38.40 | 1.20 |
| 2 | 87.12 | 1.37 |
| 3 | 175.68 | 2.01 |

Similarly, preparative scale size exclusion chromatography is an alternative method to fractionate a polymer sample into molecular weight components. Fractional precipitation of the silicone oil may also be used to separate components of the product polymer.

Removal of silicone oil components that dissolve into the bulk IOL material over time (e.g., during storage) may also be accomplished by exposing the silicone oil to bulk quantities of the IOL material, or other materials that have been selected for that purpose. On storage with an appropriate material, the components of the silicone oil that dissolve into the bulk IOL polymeric material may be removed by adjusting the ratio of silicone oil to polymer adsorbent so that sufficiently low levels of those materials remain in the oil.

An important aspect of the fractionated oils herein is the very low polydispersity ("PDI") (e.g., less than 1.5, less than 1.3, or even less than 1.2) that has not be able to be achieved with other known polymerization processes. One way to achieve the desired properties, previously unattainable, is to fractionate the oil after synthesis to eliminate the very low molecular weight portion (and potentially the very high molecular weight portion as well). A very low PDI provides the advantage of matching materials properties to performance characteristics; particularly high molecular weight (thus low swelling & power stability) and low viscosity (thus fast response time for accommodating and disaccommodating). An additional benefit of some embodiments herein that include blended high- and low-refractive index oil components, such as in Tables 5 and 6 below (e.g., blended dimethyl siloxane vs. diphenyl siloxane), is that although the fractionated oils have higher molecular weights, the blended index-matched system (index matched with the polymeric material of the lens) actually does not increase much in viscosity due to the change in blending ratios working with the inherent viscosity changes as a function of the content of the components (e.g., oil components being dimethyl siloxane and diphenyl siloxane).

Tables 6 and 7 show examples of unfractionated and fractionated blends (of high RI and lower RI), respectively, of exemplary silicone oils. The exemplary blended oils in Tables 5 and 6 have viscosities less than 1000 cPs, and blended Refractive Indexes between 1.47 and 1.50.

TABLE 5

| | Mn | Mw | PDI | RI | Visc (cPs) | Wt Fract | Calc. Visc. Blend | Calc. RI Blend | Mn | Mw | PDI |
|---|---|---|---|---|---|---|---|---|---|---|---|
| M2, High RI, R02914 | 7383 | 8842 | 1.20 | 1.4876 | 820 | 0.707 | 664 | 1.4832 | 6490 | 7766 | 1.20 |
| M2, Low RI, R02913 | 6534 | 7902 | 1.21 | 1.4726 | 409 | 0.293 | | | | | |

TABLE 6

| | Mn | Mw | PDI | RI | Visc (cPs) | Wt Fract | Calc. Visc. Blend | Calc. RI Blend | Mn | Mw | PDI |
|---|---|---|---|---|---|---|---|---|---|---|---|
| M2, Fract, High RI, GA15558 | 8814 | 9902 | 1.12 | 1.4914 | 1193 | 0.506 | 785 | 1.4832 | 8817 | 9917 | 1.12 |
| M2, Fract, Low RI, GA15564 | 7759 | 8857 | 1.14 | 1.4748 | 524 | 0.494 | | | | | |

One exemplary manner in which to create an oil with a very low PDI is by utilizing a robust, reliable, reproducible, scalable, high precision, etc., fractionation process. The fractionation process can allow for creating otherwise unattainable property matching of the silicone fluids to the lens acrylic materials, thereby minimizing swelling-induced power shifts while retaining desirable low viscosity fluids which allow acceptably fast response times, both of which are described herein.

An exemplary process is a hot isopropyl alcohol/water fractionation. The only reagents used are isopropyl alcohol and water, which can be evaporated off the oil.

In exemplary embodiments the oil includes blended dimethyl siloxane and diphenyl siloxane, examples of which are described herein, such as in the Tables. In some embodiments the oil comprises copolymers of dimethyl siloxane and diphenyl siloxane, and in some embodiments the ratio of the two can vary from 1:1 to 3:1.

Table 7 lists exemplary silicone oils, including the mean molecular weight, polydispersity, and expected diffusion. The polydispersities of these examples are all under 1.3, which is an example of under 1.5.

TABLE 7

| Name | $M_n$ | $M_w$ | PDI | <4K (%) | <3K (%) |
|---|---|---|---|---|---|
| 1:30 precipitate | 9120 | 10375 | 1.14 | 1 | 0.4 |
| 1:15 precipitate | 7836 | 8895 | 1.14 | 3 | 0.5 |
| high MW (low diff) oil | 8925 | 10310 | 1.16 | 3 | 0.5 |
| fractionation starting oil | 6951 | 8502 | 1.22 | 7 | 3 |
| M2 | 6791 | 8094 | 1.19 | 8 | 3 |
| 1:30 supernatant | 6044 | 7125 | 1.18 | 12 | 5 |
| 1:15 supernatant | 4924 | 5944 | 1.21 | 24 | 9 |

Table 8 lists exemplary silicone oils, including mean molecular weight, polydispersity, and change in power. The polydispersities of these examples are all under 1.3, which is an example of under 1.5.

TABLE 8

| Sample ID | Mn Avg | Mw Avg | PDI Avg |
|---|---|---|---|
| #13 | 6497 | 7816 | 1.20 |
| R01457 | 6659 | 7899 | 1.19 |
| R01108 | 6797 | 8003 | 1.18 |
| R01349 | 6827 | 8030 | 1.18 |
| R01096 | 6796 | 8099 | 1.19 |
| R01456 | 6971 | 8220 | 1.18 |
| R00934 | 7076 | 8362 | 1.18 |
| #12 | 7251 | 8457 | 1.17 |
| #11 | 8917 | 10309 | 1.16 |
| Fractionated | 9120 | 10375 | 1.14 |

In some embodiments the mean molecular weight of the oil is about 4500 Da to about 6500 Da, and in some embodiments is between 5000 Da and 6000 Da, such as about 5200 Da and 5800 Da. In some embodiments the viscosity is less than 2400 cPs.

While silicone oils used in accommodating IOLs are primarily described herein, it is possible to use any of the silicone oils in a non-accommodating IOL. For example, a non-accommodating IOL can have a relatively rigid outer polymeric shell surrounding a silicone oil core. Swelling of the bulk polymeric material would still need to be taken into consideration, and hence the methods of manufacturing desired silicone oil described herein could be utilized.

In some embodiments in U.S. Pub. No. 2013/0131794, the accommodating intraocular lenses include an optic portion including an anterior lens element and a posterior lens element that define an optic fluid chamber. While in some embodiments the fluid can be substantially index matched with the material of the anterior and posterior elements (essentially creating an optic that behaves like a single lens), in some embodiments the fluid has a different refractive index than one or both of the anterior lens element and the posterior lens element. By having a fluid in the optic chamber that has a different refractive index, two additional optical interfaces can be created within the optic portion (anterior lens element/fluid interface, and the fluid/posterior lens element interface). By having additional optical interfaces, it is possible to provide more control over the power of the IOL throughout the accommodative process.

The invention claimed is:

1. An adhesive formulation, comprising:
   trifluoroethyl methacrylate;
   at least one of butyl acrylate and n-butyl methacrylate;
   at least one of phenylethyl acrylate and phenylethyl methacrylate; and
   a reactive acrylic monomer diluent,
      wherein the reactive acrylic monomer diluent is 23% to 43% of the adhesive formulation, and
      wherein the reactive acrylic monomer diluent is 1-adamantyl methacrylate (ADMA).

2. The adhesive formulation of claim 1, further comprising a UV blocker.

3. The adhesive formulation of claim 1, further comprising a photoinitiator.

4. The adhesive formulation of claim 3, wherein the photoinitiator is 2% of the adhesive formulation.

5. The adhesive formulation of claim 1, wherein the adhesive is configured to be cured by UV light.

6. The adhesive formulation of claim 1, further comprising hydroxyl ethyl acrylate.

7. An adhesive formulation, comprising:
   a first component comprising monomers, wherein the monomers comprise:
      butyl acrylate or n-butyl methacrylate, wherein the butyl acrylate or n-butyl methacrylate is between 35% to 45% of the first component,
      phenylethyl acrylate or phenylethyl methacrylate, and wherein the phenylethyl acrylate or the phenylethyl methacrylate is between 20% to 40% of the first component,
      trifluoroethyl methacrylate, and wherein the trifluoroethyl methacrylate is between 15% to 30% of the first component; and
   a second component comprising a reactive acrylic monomer diluent, wherein the second component comprises between 23% to 43% of the adhesive formulation.

8. The adhesive formulation of claim 7, wherein the first component is a cross-linkable polymer.

9. The adhesive formulation of claim 7, wherein the first component comprises between 55% to 75% of the adhesive formulation.

* * * * *